US012016686B2

(12) United States Patent
Isensee

(10) Patent No.: US 12,016,686 B2
(45) Date of Patent: *Jun. 25, 2024

(54) FULLY IMPLANTABLE SENSOR ELEMENT AND METHOD FOR DETECTING AT LEAST ONE ANALYTE IN A BODY FLUID

(71) Applicant: Roche Diabetes Care, Inc., Indianapolis, IN (US)

(72) Inventor: Katharina Isensee, Heidelberg (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 662 days.

This patent is subject to a terminal disclaimer.

(21) Appl. No.: 17/135,387

(22) Filed: Dec. 28, 2020

(65) Prior Publication Data
US 2021/0137430 A1    May 13, 2021

Related U.S. Application Data

(63) Continuation of application No. PCT/EP2019/066853, filed on Jun. 25, 2019.

(30) Foreign Application Priority Data

Jun. 29, 2018 (EP) .................................. 18180711

(51) Int. Cl.
*A61B 5/1455* (2006.01)
*A61B 5/145* (2006.01)
(Continued)

(52) U.S. Cl.
CPC ........ *A61B 5/14546* (2013.01); *A61B 5/1459* (2013.01); *H01S 5/3402* (2013.01); *A61B 2562/0233* (2013.01)

(58) Field of Classification Search
CPC .............. A61B 5/1455; A61B 5/14551; A61B 5/14552; A61B 5/14532; A61B 5/14546; A61B 5/1459; A61B 5/0031; A61B 5/686
See application file for complete search history.

(56) References Cited

U.S. PATENT DOCUMENTS 6,410,309 B1 *  6/2002  Barbera-Guillem ... C12M 23/22
                                                      435/297.5
6,421,548 B1    7/2002  Berman et al.
(Continued)

OTHER PUBLICATIONS

International Search Report and Written Opinion of the International Searching Authority, PCT/EP2019/066853, Nov. 7, 2019, 17 pages.

(Continued)

*Primary Examiner* — Chu Chuan Liu
(74) *Attorney, Agent, or Firm* — Bose McKinney & Evans LLP

(57) ABSTRACT

A fully implantable sensor for detecting an analyte in a body fluid sample is disclosed. The sensor includes a chamber plate that receives the body fluid sample. The chamber plate has a biocompatible polymer membrane having a molecular weight cutoff of at least 15 kDa. The sensor also includes a quantum cascade laser illumination source that generates an illumination light beam in a spectral range and transmits the light beam to the chamber plate. In response to the illumination light beam at least partially illuminating the chamber plate, the chamber plate generates a reflection light beam that at least partially illuminates the body fluid sample within the chamber plate. The sensor has an optical detector that detects at least one property of the reflection light beam and generates a sensor signal that correlates to the presence of the analyte. The sensor includes a controller to evaluate the sensor signal.

15 Claims, 4 Drawing Sheets

(51) Int. Cl.
  *A61B 5/1459*    (2006.01)
  *H01S 5/34*      (2006.01)

(56) References Cited

U.S. PATENT DOCUMENTS

| | | | |
|---|---|---|---|
| 8,040,526 B2 | 10/2011 | Kiesel et al. | |
| 2007/0004974 A1 | 1/2007 | Nagar et al. | |
| 2007/0150019 A1* | 6/2007 | Youker | A61N 1/3787 607/29 |
| 2008/0231857 A1 | 9/2008 | Depeursinge et al. | |
| 2010/0121163 A1 | 5/2010 | Vestel et al. | |
| 2011/0082353 A1 | 4/2011 | Kiesel et al. | |
| 2012/0059232 A1 | 3/2012 | Gross et al. | |
| 2014/0294914 A1* | 10/2014 | Olson | A61F 2/14 424/93.4 |

OTHER PUBLICATIONS

Puspasari et al., Charge- and Size-Selective Molecular Separation using Ultrathin Cellulose Membranes, ChemSusChem, vol. 9, No. 20, Aug. 30, 2016, pp. 2908-2911.

Kim et al., Miniaturized mid-infrared sensor technologies, Analytical and Bioanalytical Chemistry, vol. 390, No. 1, Nov. 10, 2007, pp. 231-237.

Vrančić et al., Continuous glucose monitoring by means of mid-infrared transmission laser spectroscopy in vitro, Analyst, vol. 136, No. 6, Jan. 27, 2011, pp. 1192-1198.

Vrančić et al., A Quantitative Look Inside the Body: Minimally Invasive Infrared Analysis in Vivo, Anal. Chem., 2014, 86, pp. 1836-1845.

\* cited by examiner

FULLY IMPLANTABLE SENSOR ELEMENT AND METHOD FOR DETECTING AT LEAST ONE ANALYTE IN A BODY FLUID

RELATED APPLICATIONS

This application is a continuation of PCT/EP2019/066853, filed Jun. 25, 2019, which claims priority to EP 18 180 711.6, filed Jun. 29, 2018, the entire disclosures of both of which are hereby incorporated herein by reference.

BACKGROUND

This disclosure relates to an implantable sensor element and a kit for detecting at least one analyte in a body fluid as well as to a method for detecting at least one analyte. The devices and methods according to the present disclosure may mainly be used for long-term monitoring of an analyte concentration in a body fluid, such as for long-term monitoring of a glucose level or of the concentration of one or more other types of analytes in a body fluid. This disclosure may both be applied in the field of home care and in the field of professional care, such as in hospitals. Other applications are feasible.

Monitoring certain body functions, more particularly monitoring one or more concentrations of at least one metabolite concentration in a body fluid plays an important role in the prevention and treatment of various diseases. Such metabolites can include by way of example, but not exclusively, blood glucose, lactate, cholesterol or other types of analytes and metabolites. Without restricting further possible applications, the disclosure will be described in the following text with reference to blood-glucose monitoring. However, additionally or alternatively, this disclosure can also be applied to other types of analytes.

Conventional devices for determining analyte concentrations are in many cases based on generating a sample of a body fluid, for example a drop of blood, which is then tested with respect to its analyte content. Continuous surveillance of the body's glucose concentration can significantly improve the treatment and prevention of long-term complications of diabetes patients. Typically devices for continuous glucose monitoring are meant for minimally-invasive short-term use, for example shorter than 14 days, and are based on an electrochemical detection scheme, in particular on the enzymatic digestion of glucose. Transcutaneous sensor systems typically imply a large number of technical challenges. Thus, a first challenge resides in the fact that the lifetime of a sensor is limited. A sensor is generally worn for approximately one week. After that, influences such as enzymes being used up and/or a sealing off in the body generally reduce the sensitivity of the sensor, or it is expected that the sensor fails. However, long-term continuous glucose monitoring, for example for terms of around one year, is desirable for several applications. Sensors for long-term monitoring based on optical systems are an area of current research.

Optical systems generally use at least one sensor material which changes at least one optically measurable property in the presence of one or more specific analytes. Alternatively, absorption methods may be used. For example, U.S. Publication No. 2007/0004974 describes an apparatus for assaying an analyte in a body comprising: at least one light source implanted in the body controllable to illuminate a tissue region in the body with light of at least one wavelength that is absorbed by the analyte and as a result generates photoacoustic waves in the tissue region; at least one acoustic sensing transducer coupled to the body that receives acoustic energy from the photoacoustic waves and generates signals responsive thereto; and a processor that receives the signals and processes them to determine a concentration of the analyte in the illuminated tissue region.

In principle, sensors based on mid-infrared technology may be used for long-term continuous glucose monitoring. Mid-infrared radiation can be used for excitation of fundamental oscillation modes of biomolecules, such as for quantitative determination of glucose. Beside spectroscopic detection of glucose using photoacoustic and photothermic methods, quantitative determination of glucose may be performed via absorption spectroscopy. However, major challenges for in vivo measurements using mid-infrared radiation absorption spectroscopy are skin heterogeneity and the high absorption coefficient of water, because typically the relative change of absorption spectrum due to glucose concentration is small.

Quantum cascade lasers (QCLs) are known as mid-IR radiation source with uniquely high spectral power density. Because of high spectral power density of QCLs the high absorption coefficient of water can be overcome by using QCLs and, thus, allowing quantitative determination of glucose. For example, C. Vrančić et al., "Continuous glucose monitoring by means of mid-infrared transmission laser spectroscopy in vitro," Analyst, 2011, 136, 1192-1198 and C. Vrančić et al., "A Quantitative Look Inside the Body: Minimally Invasive Infrared Analysis in Vivo," Anal. Chem., 2014, 86 1836-1845 describe implantable fiber-based sensors using mid-infrared laser spectroscopy. Such fiber-based sensors comprise a fiber transmitting light in the mid-infrared spectral range and having a central cavity as measurement volume. Molecules of interstitial fluid are transported via diffusion into the measurement volume and can be determined quantitatively via an absorption measurement.

U.S. Pat. No. 8,040,526 B2 describes an implantable product which includes an optical cavity structure with first and second parts, each of which can operate as an optical cavity. The first part includes a container with at least one opening through which bodily fluid can transfer between the container's interior and exterior when the product is implanted in a body. The second part includes a container that is closed and contains a reference fluid. The implantable product can also include one or both of a light source component and a photosensing component. Photosensed quantities from the first part's output light can be adjusted based on photosensed quantities from the second part's output light. Both parts can have their light interface surfaces aligned so that they both receive input light from a light source component and both provide output light to a photosensing component.

U.S. Publication No. 2012/059232 A1 describes an apparatus including a support configured to be implanted within a body of a subject and a sampling region coupled to the support. The apparatus is configured to passively allow passage through the sampling region of at least a portion of fluid from the subject. The apparatus also includes an optical measuring device in optical communication with the sampling region. The optical measuring device comprises at least one light source configured to transmit light through at least a portion of the fluid, and at least one sensor configured to measure a parameter of the fluid by detecting light passing through the fluid.

U.S. Publication No. 2008/231857 A1 describes a sensor system for detection of a gaseous chemical substance, which includes an optical sampling cell holding a sampling chamber of a volume of at most 20 mm$^3$, a light emitter and a light receiver. The sampling cell is adapted for free-space, single monomodal propagation of the light beam.

U.S. Publication No. 2010/121163 A1 describes optical microneedles which are adapted for near-infrared or mid-infrared in vivo spectroscopic sensing and provide a MEMS-based spectrometer for continuous lactate and glucose monitoring by means of a near-infrared or mid-infrared optical microneedle array in a transdermal patch.

Tiara Puspasari et al.: "Charge- and Size-Selective Molecular Separation using Ultrathin Cellulose Membranes," CHEMSUSCHEM, vol. 9, no. 20, August 39, 2016, pages 2908-2911, XP055513471, DE ISSN: 1864-5631, DOI:10.1002/cssc.201600791 describes application of cellulose membranes for selective separation of small molecules. It describes a freestanding cellulose membrane as thin as 10 nm that has been prepared through regeneration of trimethylsilyl cellulose (TMSC). The freestanding membrane can be transferred to any desired substrate.

However, despite the advantages of such known fiber-based sensors, fiber-based sensors have considerable disadvantages in practice. Optical fibers in practice have considerable sensitivity to mechanical influences, for example due to mechanical loads during implantation and/or removal and during wearing and monitoring in the body. For example, a measurement signal may be susceptible for mechanical instabilities using an optical fiber as guide for radiation. Furthermore, sensor design of known fiber-based sensors leads to at least two permanent injuries of the skin for implantation which may limit wearing comfort and may permit ingress of contaminations, such as germs or other substances, into the organism which may cause infections. In addition, known fiber-based sensors require filtration of interstitial fluid for quantitative determination of glucose via infrared absorption spectroscopy in order to ensure functionality of the sensor. The measurement volume has to be membrane shielded and protected from macromolecules, for example, by using a semipermeable membrane. However, implementation of such a membrane into the sensor design of known fiber-based sensors is difficult without increasing diffusion course and thus worsening response behavior of the sensor. Further, availability of such membranes is limited. Furthermore, known infrared fibers such as chalcogenide fibers, coated hollow fibers and silver halide fibers are cytotoxic and require an, e.g., polyethylene coating in order to be used in the body.

SUMMARY

This disclosure teaches an implantable sensor element and methods for determining at least one analyte in a sample of body fluid, which avoid the above-described disadvantages of known sensors and methods. In particular, the implantable sensor element allows reliable reagent-free continuous monitoring of glucose in a sample of body fluid and mechanical stability such as enhanced wearing comfort and reduced ingress of contaminations.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "chamber plate," "illumination source," "detector" and "membrane," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of the present disclosure, a fully implantable sensor element for detecting at least one analyte in a sample of body fluid is disclosed.

The fully implantable sensor element comprises at least one measurement chamber plate adapted to receive the sample of bodily fluid. The fully implantable sensor element comprises at least one illumination source designed to generate at least one illumination light beam in at least one spectral range and to transmit the illumination light beam to the measurement chamber plate such that the illumination light beam at least partially illuminates the measurement chamber plate. The measurement chamber plate is designed to generate at least one reflection light beam in response to the illumination by the illumination light beam such that the reflection light beam at least partially illuminates the sample of body fluid within the measurement chamber plate. Preferably, the sample of body fluid may be illuminated at least twice within the measurement chamber plate. The sample may be illuminated, firstly, by the illumination light beam, for example in a first direction, and, subsequently, by the reflection light beam, for example, in a second direction. The fully implantable sensor element comprises at least one optical detector designed to detect at least one property of the reflection light beam and to generate at least one sensor signal dependent on the presence of the analyte. The fully implantable sensor element furthermore comprises at least one control unit designed to evaluate the sensor signal. The illumination source comprises at least one quantum cascade laser. The measurement chamber plate comprises at least one biocompatible polymer membrane having a molecular weight cutoff of at least 15 kDa. The biocompatible polymer membrane may have a molecular weight cutoff of 15 kDa or greater. For example, the molecular weight cutoff may be 25 kDa.

As used herein, the term "implantable" refers to the fact that the sensor element is adapted to have appropriate dimensions to be inserted into the body tissue of the user, such as into subcutaneous tissue, and, further, that the sensor element is biocompatible in order to remain in the body tissue for an elongated time period, such as for several days or even several weeks or several months. Thus, as an example, the sensor element may have a biocompatible coating and/or may be biocompatible. The term "implant" refers to the fact that the sensor element may be inserted fully or partially into the body tissue. Thus, in the following, the terms "implant" and "insert" will be used as synonyms. The sensor element is a fully implantable sensor element. The term "fully implantable" further refers to the design of the sensor element such that all parts of the sensor element can be fully implanted into the body tissue, in particular without any part of the sensor element protruding through the skin of the user, i.e., a full subcutaneous implantation. Generally, during implantation and/or during use of the sensor element, the sensor element may fully or partially penetrate the skin of the user. Thus, the sensor element preferably may be embodied as a fully implantable transcutaneous sensor element.

As used herein, the term "sensor element" generally refers to a unit, which may be handled as one entity, comprising the at least one measurement chamber plate, at least one illumination source, at least one optical detector and at least one control unit. The sensor element may be adapted to perform at least one absorption measurement.

As used herein, the term "detecting" refers to a quantitative and/or qualitative determination of an analyte concentration, i.e., a determination of the amount and/or concentration of the analyte in the body fluid and/or the response to the question of whether the analyte is present in the body fluid. As further used herein, the term "analyte" may refer to an arbitrary element, component or compound which may be present in a body fluid and the concentration of which may be of interest for a user. Preferably, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Additionally or alternatively, however, other types of analytes may be used and/or any combination of analytes may be determined. As generally used within the present disclosure, the term "user" may refer to a human being or an animal, independent from the fact that the human being or animal, respectively, may be in a healthy condition or may suffer from one or more diseases. As an example, the user may be a human being or an animal suffering from diabetes. However, additionally or alternatively, the disclosure may be applied to other types of users.

Generally, an arbitrary type of body fluid may be used. Preferably, the body fluid is a body fluid which is present in a body tissue of the user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue. Thus, generally, the detection of the at least one analyte in the body fluid may preferably be determined in vivo.

The fully implantable sensor element comprises at least one measurement chamber plate adapted to receive the sample of bodily fluid. As used herein, the term "measurement chamber plate" refers to an element adapted to receive the sample of body fluid having a sheet or plate-like geometry. The measurement chamber plate may have a flat geometry. The measurement chamber plate may comprise a monolithic or a multi-plate setup. The sheet or plate-like structure geometry may enhance mechanical stability and thus robustness of a measurement signal. As further used herein, the term "receive" the sample of body fluid refers to the fact that the measurement chamber plate is adapted to one or more of permitting ingress of body fluid, contacting with body fluid and being in exchange with the body fluid. The measurement chamber plate may be designed such that the analyte concentration within the measurement chamber is adjusted and/or adapted, for example, by diffusion processes, to the analyte concentration of the ambient body fluid. The measurement chamber plate may receive the sample of body fluid via diffusion processes. Filling the sample via diffusion processes may ensure maintenance-free operation of the implanted sensor element. The measurement chamber plate may comprise at least one hydrogel as diffusion permeable material. The hydrogel may be arranged between the chamber walls, specifically in order to achieve a filtering effect such that ingress of large sized molecules can be prevented. In addition, the hydrogel may be arranged within holes of a silicon membrane, which will be described below, such that the hydrogel may function as a membrane within the pores of the silicon membrane.

The measurement chamber plate is designed to generate at least one reflection light beam in response to the illumination by the illumination light beam such that the reflection light beam at least partially illuminates the sample of body fluid within the measurement chamber plate. Preferably, the sample of body fluid is illuminated by the illumination light beam before the sample of body fluid is illuminated by the reflection light beam. The reflection light beam may be adapted to illuminate the sample of body fluid. The reflection light beam may illuminate a volume of the sample of body fluid. As used herein, the term "reflection light beam" refers to at least one light beam reflected by the measurement chamber plate. The measurement chamber plate may comprise at least one reflector element and/or may comprise a reflective material such as a reflective coating. The measurement chamber plate may be adapted to at least partially reflect the illumination light beam. The term "at least partially reflect" refers to a complete or partial reflection of the illumination light beam. For example, the measurement chamber plate, in particular at least one reflector of the measurement chamber, may be adapted to reflect more than 20% of the illumination light beam, preferably more than 50% of the illumination light beam, most preferably more than 80% of the illumination light beam. As further used herein, the term "at least partially illuminates the sample of body fluid" refers to the fact that the reflection light beam may completely or partially illuminate the sample of body fluid. For example, the reflection light beam may illuminate more than 5% of the sample of body fluid, preferably more than 10%, more preferably more than 25% of the sample of body fluid. However, embodiments are feasible. The measurement chamber plate may be designed such that the reflection light beam illuminates a volume of the sample as large as possible.

The measurement chamber plate may comprise at least one membrane element. The membrane element may be adapted to protect the measurement chamber plate from penetration of particles above a certain size such as large sized molecules like proteins and/or cells like leukocytes.

The measurement chamber plate may comprise at least one chamber wall, wherein the chamber wall is adapted to receive the sample of body fluid. The sensor element may be adapted to perform at least one measurement based on absorption spectroscopic techniques using a miniaturized fluid cell. The measurement chamber plate may be adapted to receive a sample size of body fluid such that a reliable absorption measurement can be performed. For example, a layer thickness of body fluid in the measurement chamber plate may be between 1 µm and 100 µm, preferably between 5 µm and 50 µm, more preferably the layer thickness may be between 8 µm and 15 µm. For example, the layer thickness may be 10 µm in order to ensure high sensitivity to detect glucose in aqueous solution. The chamber wall may be adapted to have a first side at least partially permeable to light, for example in the infrared spectral range, and a second side at least partially permeable to the sample of body fluid. As used herein, "permeable to light" refers to the capability to at least partially permit a light beam, for example, the illumination light beam and/or the reflection light beam, to pass through. Thus, the first side of the chamber wall may be at least partially transparent. As used herein, "permeable to the sample of body fluid" refers to the capability to at least partial permit ingress into and/or permit pass through of the sample of body fluid into the measurement chamber wall. The chamber wall may be arranged such that the side permeable to the sample of body fluid faces an exterior of the sensor element.

For example, the measurement chamber plate may comprise at least one first chamber wall adapted to be at least partially transparent to the illumination light beam. The first chamber wall may be designed as at least one at least partially transparent first infrared window. The first chamber wall may be arranged facing an interior of the sensor element such as an interior surrounded by a housing of the sensor element. The first chamber wall may face the illumination light beam. The first infrared window may be designed to let, at least partially, the illumination light beam through the infrared window to the sample of body fluid. For example, the infrared window may be designed to let, at least partially, the illumination light beam pass through the infrared window into the measurement chamber plate. The first chamber wall may be designed as transmission window. The first chamber wall may be a light-permeable inner plate. The first chamber wall may be biocompatible. The first chamber wall may comprise and/or may be produced from at least one biocompatible material. The first chamber wall may consist fully of biocompatible material, for example a biocompatible material comprising at least one synthetic diamond or silicon. The first chamber wall may comprise at least one anti-reflective coating adapted to minimize reflections from a surface of the first chamber wall to the optical detector and/or reflections of the reflected beam back into the measurement chamber plate, for example, in order to minimize interference effects on the signal. The first chamber wall may comprise at least one micro-structured surface, e.g., roughened surface adapted to minimize reflections from a surface of the first chamber wall to the optical detector and/or reflections of the reflected beam back into the measurement chamber plate, for example, in order to minimize interference effects on the signal. The first chamber wall, additionally or alternatively, may comprise an anti-reflective coating arranged on the side of the first chamber wall facing the water.

The measurement chamber plate may comprise at least one second chamber wall adapted to at least partially receive the sample of body fluid. The second chamber wall may be a fluid-permeable outer plate. The measurement chamber plate may comprise at least one capillary element arranged between the first chamber wall and the second chamber wall. The capillary element may be adapted to receive the sample of body fluid. As used herein, the term "capillary element" generally refers to an element which forms at least a part of a cuvette, cell or cavity for receiving and/or storage of the sample of body fluid. The receiving of the sample of body fluid may be supported by capillary forces. The first and the second chamber walls may be arranged at opposing sides of a capillary element and form a measurement cuvette. The capillary element may be designed to receive an amount of body fluid required for reliable determination of the analyte. In order to obtain a maximum sensitivity of glucose in aqueous solution, the capillary element may be designed to receive a fluid layer thickness between 1 to 100 µm, preferably between 5 µm and 50 µm, more preferably between 8 µm and 15 µm. For example, the capillary element may be designed to receive a fluid layer thickness of 10 µm. The capillary element may receive the sample of body fluid via diffusion processes. In order to ensure suitable sensor response behavior, the capillary element may be designed such that diffusion distances are as short as possible, preferably around 100 µm.

The measurement chamber plate may comprise at least one spacer element arranged between the first chamber wall and the second chamber wall. As used herein, the term "spacer element" refers to an arbitrary shaped element adapted to adjust a distance between the first and second chamber walls. The spacer element may have an arbitrary shape, for example, the spacer element may be at least one ring. The spacer element may have a thickness between 1 and 100 µm. The spacer element may be a cut polyester film. Additionally or alternatively, one of the first and the second chamber walls may comprise at least one cavity and/or recess, for example produced by photolithographic methods, adapted to form a capillary element.

The second chamber wall may be designed to be rigid against mechanical influence, for example, during assembling of the sensor element, such that a constant measurement volume can be ensured. The second chamber wall may be designed to be permeable to the analyte, for example, to glucose, such that the analyte can reach the measurement chamber plate. The second chamber wall may be designed to prevent large-sized molecules and/or cells to penetrate into the measurement chamber plate. The second chamber wall may be different from the biocompatible polymer membrane, specifically, the second chamber wall and the biocompatible polymer membrane may be designed as separate elements.

The second chamber wall may be designed as at least one at least partially reflective second infrared window. The second infrared window may comprise at least one reflective layer, for example a gold layer. The reflective layer may be arranged on at least one side of the second infrared window facing the illumination light beam in order to enhance reflection of the illumination light beam. The second infrared window may be designed to permit transport, for example by diffusion, of the analyte into the capillary element. The second infrared window may be a fluid-permeable outer plate. The second infrared window may comprise a plurality of holes. The second infrared window may comprise a plurality of micro fluid channels. For example, the holes may be drilled micro holes having diameter less than 100 µm, preferably less than 20 µm, more preferably less than 10 µm. An average distance between two holes may be less than 500 µm, preferably less than 200 µm, more preferably less than 100 µm. A thickness of the second infrared window may be less than 1000 µm, preferably less than 500 µm. Such dimensions may ensure short diffusion times of glucose from interstitial fluid into the capillary element. The holes may have other shapes such as, for example, slits or bendings. The holes may be produced using laser processing techniques or other methods known in the art, for example, wet etching. The second infrared window may be or may comprise a silicon plate having a plurality of holes. Such a design can ensure proper rigidity. The silicon plate may be sputtered with a gold layer in order to enhance reflectivity. The second chamber wall may have a hydrophilic surface structure on one side and/or on the other side and/or in the holes of the wall adapted to have better fluidic properties. This hydrophilic surface may be made by a microfabricated surface, for example, by photo-lithographic or wet etching methods.

As outlined above, the measurement chamber plate comprises at least one biocompatible polymer membrane having a molecular weight cutoff of at least 15 kDa. The biocompatible polymer membrane may be designed as one or more flat membrane elements. The flat plate design of the measurement chamber plate may allow simple mounting of the flat membrane element. In case of using the flat membrane element, the diffusion distance may be enhanced only slightly by the thickness of the flat membrane. The further membrane element may be arranged on the side of the second infrared window and/or of the membrane element receiving the sample of body fluid. The biocompatible polymer membrane may be arranged on an outer side of the second chamber wall. The biocompatible polymer membrane and the second chamber wall may be designed as separate elements. The biocompatible polymer membrane may be non-flexible. The biocompatible polymer membrane may be configured as rigid element. As used herein, the term "membrane" generally refers to a selective barrier. Specifically, a selective barrier which allows fluids to pass and is configured for filtering of molecules and particles above a certain size. As used herein, the term "biocompatible membrane" refers to a membrane compatible with living tissue or a living system. Specifically, the biocompatible membrane is not one or more of toxic, injurious, or physiologically reactive and/or does not cause immunological rejections. As used herein, the term "molecular weight cutoff" refers to a minimum molecular weight of globular molecules which is retained to 90% by the membrane. The biocompatible polymer membrane may comprise at least one polymer selected from the group consisting of: cellulose hydrate; nitrocellulose; polysulfone; polycarbonate, preferably a capillary pore membrane; polyethersulfone; cellulose acetate; polyamide; polytetrafluoroethylene. The polymer may be hydrophilized. Cellulose hydrate is also known as regenerated cellulose to the skilled person. Thus, the biocompatible polymer membrane may be and/or may comprise regenerated cellulose. Polysulfone may be obtainable by polymerization of Bisphenol A and 4,4'-Dichlorodiphenyl sulfone. Polyethersulfone may be obtainable by polymerization of 4,4'-Dichlorodiphenyl sulfone and 4,4'-Dihydroxydiphenyl sulfone. Polyamide is also known as Nylon. The polyamide may be selected from the group consisting of polyamide 6, polyamide 6,6, polyamide 6,12 and polyamide 12. The biocompatible polymer membrane may have a pore size in a range from 15 to 35 Å. The term "pore size" refers to a median or mean size of pores on a membrane surface. The biocompatible polymer membrane may have a thickness in a range from 1 to 250 µm, preferably from 20 to 250 µm. For example, in the case of a regenerated cellulose, the thickness may be from 20 to 50 µm. The biocompatible polymer membrane may be configured for preventing ingress of macromolecules and cells into the sensor element. The biocompatible polymer membrane may prevent blocking of the measurement chamber due to ingress of macromolecules and cells. The biocompatible polymer membrane may prevent damage of the sensor element, specifically of the measurement chamber, due to ingress of macromolecules and cells. The biocompatible polymer membrane may be configured for reducing influence from proteins on the absorption measurement. Usage of the biocompatible polymer membrane may allow stable reflectivity and a thickness of the absorption layer over a long period of time and, thus, stable glucose sensitivity. Additional to the biocompatible polymer membrane, the holes of the second infrared window may be designed such that the second infrared window functions as membrane. Additionally, specifically in order to achieve biocompatibility and/or to provide the membrane with required hydrophilic properties, the biocompatible polymer membrane may have a coating on an outer side of the biocompatible polymer membrane, specifically on the side facing the tissue or body fluid.

The second chamber wall may comprise the at least one biocompatible polymer membrane. The second chamber wall may be designed as membrane element. Additionally or instead of the second infrared window, the second chamber wall may be or may comprise the at least one membrane element. The biocompatible polymer membrane and/or the second chamber wall may have reflective properties. For example, the biocompatible polymer membrane and/or the second chamber wall may comprise at least one sintered metal. The biocompatible polymer membrane and/or the second chamber wall may be sputtered with a reflective layer, such as a gold, silver or aluminum layer, to enhance reflectivity. Preferably, the reflective layer may be arranged on a side of the second chamber wall facing the measurement chamber. For example, the second chamber wall may be selected from the group consisting of a track-etched membrane comprising polycarbonate; an Anodisc membrane comprising aluminum oxide; a membrane having a supporting structure such as a polymeric microporous membrane available from Precision Membranes, LLC; a high-aspect-ratio membrane comprising silicon and/or carbon available from Precision Membranes, LLC; a porous membrane comprising sintered metal. The polycarbonate of the second chamber wall and the polycarbonate of the biocompatible polymer membrane may be different. The second chamber wall may be thicker compared to the biocompatible polymer membrane. The second chamber wall may be more rigid compared to the biocompatible polymer membrane. In one embodiment, the second chamber wall may be a membrane having a supporting structure such as a polymeric microporous membrane available from Precision Membranes, LLC. The supporting structure may be adapted to provide rigidity to the measurement chamber plate. The membrane having the supporting structure may have a thickness of several 10 µm such that the membrane element can be used as spacer element. In a further embodiment, the second chamber wall may be a high-aspect-ratio membrane comprising silicon and/or carbon available from Precision Membranes, LLC. The high-aspect-ratio membrane may have a reflective coating, for example, the membrane element may be sputtered with a gold layer. The second chamber wall may have a reflective coating, for example, the membrane element may be sputtered with a gold layer. However, embodiments without a reflective coating are feasible, e.g., a porous membrane comprising sintered metal has reflective properties in the infrared spectral range.

The measurement chamber plate may comprise at least one attenuated total reflection ("ATR") element. The attenuated total reflection element may comprise at least one ATR-crystal, for example an ATR-crystal available from ATR Elements. The ATR-crystal may comprise a structured surface. The ATR-crystal may comprise at least one microstructure adapted to receive the sample of body fluid. The microstructure may enhance amplification of the sensor signal compared to ATR-crystals without microstructures. The microstructure may be adapted as capillary, wherein the receiving of the sample of body fluid may be supported by capillary forces. The microstructure may have hydrophilic properties such that the microstructure is adapted to draw out the body fluid when in contact with the interstitial fluid. Thereby a transition layer may be formed having a fixed thickness in which the reflection measurement can be performed. The ATR-crystal may be arranged such that the illumination light beam is at least reflected once. Preferably, the illumination light beam may be reflected several times within the ATR-crystal. The illumination light beam may be collimated by the at least one transfer device, and may impinge on the ATR-crystal. The ATR-crystal may be designed such that the illumination light beam is reflected by an area of the ATR-crystal comprising the body fluid. The ATR-crystal may be biocompatible. The ATR-crystal may comprise or may be produced from biocompatible material, for example silicon or diamond. The ATR-crystal may be adapted to reflect the light beam such that it illuminates the optical detector, for example after being collimated by at least one further transfer device. At least one biocompatible membrane, specifically the biocompatible polymer membrane, may be arranged on the ATR-crystal.

The sensor element comprises at least one illumination source designed to generate at least one illumination light beam in at least one spectral range and to transmit the illumination light beam to the measurement chamber plate such that the illumination light beam at least partially illuminates the measurement chamber plate. As used herein, the term "light" generally refers to electromagnetic radiation in one or more of the visible spectral range, the ultraviolet spectral range and the infrared spectral range. The term visible spectral range generally refers to a spectral range of 380 nm to 780 nm. The term infrared (IR) spectral range generally refers to electromagnetic radiation in the range of 780 nm to 1000 μm, wherein the range of 780 nm to 2.5 μm is usually denominated as the near-infrared (NIR) spectral range, and the range from 25 μm to 1000 μm as the far-infrared (FIR) spectral range. The term mid-infrared (MIR) spectral range refers to the range from 2.5 to 25 μm. Preferably, light as used within the present disclosure is light in the mid-infrared spectral range. As used herein, the term "light beam" generally refers to an amount of light emitted into a specific direction. Thus, the light beam may be a bundle of the light rays having a predetermined extension in a direction perpendicular to a direction of propagation of the light beam.

As further used herein, the term "illumination source" refers to at least one device adapted to generate at least one light beam. As used herein, the term "illumination light beam" refers to a light beam generated by the illumination source.

The illumination source may comprise at least one light source. The illumination source may be a mid-IR radiation source. The illumination source may have a high spectral power density. The illumination source may be adapted for quantitative determination of glucose in an aqueous solution. The illumination source comprises at least one quantum cascade laser. For example, the illumination source may comprise at least one quantum cascade laser chip. The quantum cascade laser may be a miniaturized quantum cascade laser. The quantum cascade laser may be selected from the group consisting of: at least one fixed-frequency Fabry-Perot quantum cascade laser; at least one tunable external cavity quantum cascade laser; at least one distributed feedback quantum cascade laser. For example, the illumination source may comprise at least one array of quantum cascade lasers. The illumination source may be designed to be operated in pulsed or continuous mode. The sensor element may comprise at least one pulser device adapted to operate the illumination in the pulsed mode. The control unit may be adapted to control the pulser device. The sensor element may comprise at least one rechargeable energy storage device, for example at least one lithium-ion battery, adapted to supply energy to the quantum cascade laser. The quantum cascade laser may have a low power consumption such that power supply by lithium-ion battery is possible.

The illumination light beam may have a wavelength in the infrared spectral range, preferably in mid-infrared spectral range. The illumination source may be adapted to generate broadband illumination light or illumination light having a narrow bandwidth. The illumination source may be adapted to change the wavelength continuously over time. The illumination source may be adapted to generate a plurality of illumination light beams, wherein each of the illumination light beams has a different wavelength. The control unit may be adapted to perform one or more of assign, adjust or select the wavelength of the illumination light beams. For example, the illumination source may comprise at least one tunable distributed feedback quantum cascade laser and/or at least one tunable external cavity quantum cascade laser having a narrow bandwidth. The control unit may be adapted to change the wavelength continuously or non-continuously, for example, within the mid-infrared spectral range. The control unit may be adapted to adjust and/or select wavelengths suitable for identification of glucose and/or distinction of glucose from further substances in the sample of body fluid, for example substances present even after filtration, such as maltose. Additionally or alternatively, a broadband spectral range is used. For example, the illumination source may comprise at least one Fabry-Perot quantum cascade laser. In order to permit absorption measurements with a broadband illumination source, the sensor element may comprise several optical detectors and suitable spectral bandpass filters or at least one tunable optical detector having at least one tunable, spectral bandpass filter. The control unit may be adapted to rapidly switch between several different illumination light beams and/or several detectors to probe different spectral regions.

As used herein, the term "at least partially illuminates the measurement chamber plate" refers to the fact that the illumination light beam may completely or partially illuminate the measurement chamber plate. The illumination light beam may, preferably, at least partially illuminate the sample of body fluid within the measurement chamber plate. For example, the illumination light beam may illuminate more than 5% of the measurement chamber plate, preferably more than 10% of the measurement chamber plate, more preferably more than 25% of the measurement chamber plate. However, other embodiments are feasible. The illumination light beam may illuminate the measurement chamber plate under an illumination angle between 0° and 85°, preferably between 20° and 60°, more preferably between 30° and 50°. For example, the illumination angle may be 45°. The term "illumination angle" refers to an angle between an axis of incidence, i.e., a line perpendicular to a surface on which the illumination light beam impinges, and the illumination light beam.

The sensor element may comprise at least one modulation device for modulating the illumination light beam. The term "modulating of the illumination" should be understood to mean a process in which a total power of the illumination is varied, for example, with one or a plurality of modulation frequencies. For example, the modulation device may be designed for a periodic modulation, for example a periodic beam interrupting device. The modulation can be effected, for example, in a beam path between the illumination source and the measurement chamber plate. For example, the at least one modulation device may be arranged in said beam path. The modulation device may be based on an electro-optical effect. The at least one modulation device may comprise, for example, a mechanical shutter and/or a beam chopper or some other type of beam interrupting device. Alternatively or additionally, however, it is also possible to use one or a plurality of different types of modulation devices. The modulation device may comprise at least one filter element, for example at least one polarizer. In one embodiment, the illumination source itself can also be designed to generate a modulated illumination. For example, the illumination source may be embodied as a pulsed illumination source, for example as a pulsed laser. Thus, by way of example, the at least one modulation device can also be wholly or partly integrated into the illumination source.

The sensor element may comprise at least one transfer device. The transfer device may be adapted to collimate the illumination light beam and/or the reflection light beam. The transfer device may comprise at least one optical lens, such as one or more convex lenses, one or more refractive lenses, one or more collimating lenses. For example, the transfer device may be arranged such that the illumination light beam travels first through the at least one transfer device and thereafter to the measurement chamber plate. The sensor element may comprise at least one further transfer device which may be arranged such that the reflected light beam travels from the measurement chamber plate to the further transfer device until it may finally impinge on the optical detector. As used herein, the term "transfer device" refers to an optical element which may be configured to transfer the illumination light beam from the illumination source to the measurement chamber plate and/or from the measurement chamber plate to the optical detector.

The sensor element comprises at least one optical detector designed to detect at least one property of the reflection light beam and to generate at least one sensor signal dependent on the presence of the analyte. As used herein, the term "optical detector" refers to a device which is adapted for detecting at least one property of a light beam. As used herein, the term "sensor signal" generally refers to an arbitrary signal indicative of the presence of the analyte. As an example, the sensor signal may be or may comprise a digital and/or an analog signal. As an example, the sensor signal may be or may comprise a voltage signal and/or a current signal. Additionally or alternatively, the sensor signal may be or may comprise digital data. The sensor signal may comprise a single signal value and/or a series of signal values. The sensor signal may further comprise an arbitrary signal which is derived by combining two or more individual signals, such as by averaging two or more signals and/or by forming a quotient of two or more signals. The optical detector may comprise at least one photodetector. The optical detector may comprise at least one pyroelectric detector. The optical detector may comprise at least one spectrometric setting, for example at least one Fabry-Perot interferometer. The optical detector may comprise at least one analog and/or digital amplifier and/or filter in order to, for example, amplify at least one property of the reflection light beam and/or reduce noise. As used herein, the term "at least one property of the reflection light beam" refers to one or more of intensity, absorbance, attenuation, transmission, reflection, wavelength and frequency of the reflection light beam. The at least one property of the reflection light beam, for example, the intensity, may change due to the presence of the analyte and/or other substances in the sample of body fluid. The optical detector may be adapted to determine a change in intensity, for example, due to the presence of the analyte and/or other substances in the sample of body fluid. The sensor element may be adapted to perform one or more of at least one reflection measurement, at least one absorption measurement, at least one attenuated total reflectance measurement. The optical detector may be adapted to determine at least one absorption information and/or attenuation information as a function of wavelength and/or frequency of the reflection light beam. The optical detector may be adapted to determine at least one spectrum, for example, at least one absorbance spectrum, of the reflection light beam.

The sensor element furthermore comprises at least one control unit designed to evaluate the sensor signal. As used herein, the term "control unit" generally refers to an arbitrary element which is adapted to evaluate the sensor signal. The control unit may be adapted for one or more of processing, analyzing, and storing of the sensor signal. The control unit may be a central control unit. The term "data" or "measurement data" refers to both raw sensor signal and processed sensor signal. As further used within the present disclosure, the term "measurement data" refers to arbitrary data acquired by using the sensor element, indicative of the analyte concentration. The data may specifically comprise a plurality of measurement values acquired at subsequent points in time, such as over a time period of several hours, several days, several weeks or even several months. The data preferably may be acquired in an analogue or digital electronic format. The data further may be processed or pre-processed within the control unit, such as by applying at least one evaluation or pre-evaluation algorithm to the data. Thus, as an example, at least one algorithm may be applied to the data, wherein the at least one algorithm transforms primary data acquired by using the optical detector into secondary data indicating the concentration of the analyte in the body fluid, such as by applying a known or predetermined relationship between the primary data and the analyte concentration to the primary data, thereby generating secondary data. Here and in the following, no distinction will be made between primary data and secondary data. The control unit may comprise at least one evaluation device designed to evaluate the sensor signal. The evaluation device may be designed to generate at least one information on the analyte by evaluating the sensor signal. As an example, the evaluation device may be or may comprise one or more integrated circuits, such as one or more application-specific integrated circuits (ASICs), and/or one or more data processing devices, such as one or more computers, preferably one or more microcomputers and/or microcontrollers. Additional components may be included, such as one or more preprocessing devices and/or data acquisition devices, such as one or more devices for receiving and/or preprocessing of the sensor signals, such as one or more AD-converters and/or one or more filters. Further, the evaluation device may comprise one or more data storage devices. Further, the evaluation device may comprise one or more interfaces, such as one or more wireless interfaces and/or one or more wire-bound interfaces. As used herein, the term "at least one information on the analyte" refers to quantitative and/or qualitative information on the analyte. For example, the evaluation device may be adapted to determine at least one spectral information of the reflection light beam from the sensor signal. The spectral information may be at least one absorption spectrum or at least one attenuation spectrum. For example, spectra may be acquired by continuously changing the laser's wavelength over time and measuring the sensor signal on the optical detector. The difference in absorbance ΔA can be calculated using water as a reference, $I_{ref}$, by $$\Delta A = -\log\left[(I_{meas})/(I_{ref})\right],$$

with $I_{meas}$ being the sensor signal seen.

The evaluation device may be adapted to determine the analyte concentration by evaluating the spectral information. The evaluation device may be designed to identify characteristic spectral signature of molecules in the mid-infrared spectral range. The evaluation device may be adapted to compare the measured spectral information with predetermined or theoretical spectral information stored, for example, in an electronic table such as in at least one look-up table. The evaluation device may be adapted to determine from the spectral information the at least one information on the analyte by using uni- or multivariate data analysis, e.g., principle component regression (PCR) and partial least square regression (PLS). The evaluation device may be adapted to detect and potentially quantify a variety of biomolecules using uni- or multivariate data analysis. For example, the evaluation device may be adapted to determine the presence and/or concentration of glucose. The evaluation device may be adapted to identify and/or determine a relevant signal or signal component, for example a signal referring to glucose, and to distinguish the relevant signal from signals of interfering molecules. The evaluation device may be adapted to distinguish the relevant signal from other signal influences such as from signal influences due system changes such as temperature.

The control unit, for example, the evaluation device, may comprise at least one or more of amplifier circuits adapted to amplify the sensor signal and/or to transform the sensor signal into an electrical current or voltage; at least one analog-/digital converter adapted to digitalize the sensor signal, for example, the amplified sensor signal; at least one digital filter adapted to optimize a signal-to-noise ratio such as at least one Lock-In amplifier and/or at least one Boxcar integrator; at least one analog filter adapted to filter the sensor signal, for example, before digitalization; at least one memory unit adapted to store the sensor signal, for example, the raw sensor signal and/or the evaluated, for example, digitalized and/or amplified, sensor signal. As used herein, a "memory unit" generally may refer to an arbitrary device adapted for collecting and preferably storing data such as measurement data. Thus, the memory unit generally may comprise at least one data storage device such as at least one volatile and/or at least one non-volatile data storage element. The components listed above may be designed as separate components within a housing of the sensor element. Alternatively, two or more of the components as listed above may be integrated into one component. For example, the optical detector may comprise an integrated amplifier circuit and/or one or more signal filters. Additionally or alternatively, one or more of these components may be provided in a further device situated outside the body of the user. The sensor element can be adapted to transfer data, such as the raw sensor signal and/or the evaluated sensor signal, automatically and/or upon request to the further device for evaluation and data storing. The control unit can be designed to receive instructions and/or data, for example, from the further device, contactless, for example via the inductive connection. The sensor element and the further device may be adapted to communicate, i.e., transfer data and instructions, wirelessly such as by an inductive connection. Other ways of data transfer, however, are feasible. The control unit may comprise at least one communication unit for wireless communication. Read-out of the measurement data from the sensor element may be performed wirelessly such that wearing comfort and freedom of movement is enhanced.

The evaluation device may be adapted to perform a temperature correction. The sensor signal may be influenced due to temperature changes such that drifts in signal may occur. The evaluation device may be adapted to distinguish signal drift due to temperature change from signal drift due to changes in analyte concentration by using spectral information. The temperature influence may be corrected using calibration data from a prior temperature calibration measurement. Additionally or alternatively, the sensor element may comprise at least one temperature sensor such as, for example, a platinum resistance thermometer. The temperature sensor may be arranged in close proximity to the measurement chamber plate. The temperature influence may be corrected using calibration data from a prior temperature calibration measurement and the measured temperature of the temperature sensor.

The sensor element may comprise at least one housing adapted to encapsulate the further components of the sensor element such as the illumination source, the control unit and the optical detector. The housing may allow complete or at least partial implantation of the sensor element within the body of the user. Thus, the housing may prevent permanent open skin barrier and, thus, the housing may prevent penetration of bacteria and other contaminations in the body. The housing may be designed to prevent contamination of the sensor element, for example with dirt and moisture. The housing may be biocompatible in order to reduce and/or minimize specific immune reactions. The housing may comprise and/or be produced from biocompatible material. For example, the biocompatible material may comprise titanium alloy.

The sensor element may comprise at least one rechargeable energy storage device. The rechargeable energy storage device may be adapted to supply voltage for one or more of the sensor elements such as the illumination source, the control unit, in particular the amplifier circuit, and the optical detector, pulser device, etc. The control unit may be adapted to control power supply to the components of the sensor element. For example, the control unit may be adapted to control power supply to one or more of the optical detector such as to the amplifier circuit, the illumination source such as the pulser device. The rechargeable energy storage device may be adapted to be charged in a contactless fashion. For example, the rechargeable energy source may be adapted to be charged wirelessly such as by an inductive connection. Other ways of recharging, however, are feasible. Charging in a contactless fashion may allow long-term operation without surgical interventions. The rechargeable energy storage device may comprise at least one lithium-ion battery. The rechargeable energy storage device may be charged by using the further device situated outside the body of the user, such as by using a docking station or the like. For example, the further device may be designed to be worn by the user. The further device may comprise at least one further rechargeable energy storage device. The further rechargeable energy storage device may be adapted to be charged using at least one cable. The further device may be adapted to bring a demand for recharging the rechargeable energy storage device of the sensor element to a user's attention, such as in one or more of a visual fashion, an acoustic fashion or a vibrational fashion. Thus, as an example, the further device may be adapted to provide at least one of a visual indication, such as a display of an appropriate message, and/or an acoustic indication, such as a warning sound or a voice message, and/or a vibrational indication, such as a vibrational alarm, to a user, in order to indicate to the user that a recharging of the rechargeable energy storage device is required. As used herein, a "demand for recharging" generally may be or may comprise an arbitrary item of information regarding one or both of a status of charge of the at least one rechargeable energy storage and/or an information indicating that a recharging of the rechargeable energy storage device is necessary in order to maintain an operation of the sensor element. A "demand," as used in the context of the present disclosure, thus, generally may refer to an arbitrary item of information from which a necessity for recharging the rechargeable energy storage device may be deduced.

The sensor element may comprise at least one measurement channel and at least one reference channel. The measurement channel may be designed to determine the concentration of the analyte. Thus, the measurement channel may comprise at least the measurement chamber plate adapted to receive the sample of body fluid. The reference channel may be designed to determine at least one correction information. The reference channel may comprise at least one reference measurement chamber adapted to receive at least one reference sample, for example water. The reference measurement chamber may not be permeable to fluids. The reference measurement chamber may be designed to prevent ingress of the sample of body fluid into the reference measurement chamber. The reference channel may have a known or pre-determined beam path of reference illumination light beam and/or reference reflection light beam. The beam paths of the reference illumination light beam and/or reference reflection light beam may be identical or similar to the beam path of the illumination light beam and/or reflection light beam. The reference measurement chamber may have known or pre-determined layer thickness. The reference measurement chamber may have identical or similar layer setup and/or thickness compared to the measurement chamber plate. The at least one correction information may be determined simultaneously or independent from the determination of the analyte. The correction information may comprise at least one information about a drift correction and/or temperature correction. The evaluation device may be adapted to correct the measurement data in response to the correction information.

In a further aspect of the present disclosure, a kit for detecting at least one analyte in a sample of body fluid is disclosed. The kit comprises at least one implantable sensor element according to the present disclosure and at least one further device. The further device is adapted to provide energy to at least one rechargeable energy storage device. For further details concerning this aspect of the present disclosure, reference may be made to the description of the other aspects of the implantable sensor element as provided above and/or below.

As used herein, a "kit" is an assembly of a plurality of components, wherein the components each may function and may be handled independently from each other, wherein the components of the kit may interact to perform a common function. Thus, the kit may comprise a plurality of components, wherein each component may be handled individually, independent from the other components and may perform at least one function independently, wherein, further, all components or groups of components comprising at least two of the components may be combined, such as by physically connecting these components, in order to perform a common function implying functionality from the connected components. The kit comprises the above-mentioned components, i.e., the at least one implantable sensor element and the at least one further device. As used herein, the term "further device" generally may refer to an arbitrary module of the kit which may be handled independently from the sensor element. The further device may be adapted to fulfill at least one function, such as an analytical function and/or an electrical function and/or a medical function and/or computational function. The components of the kit may be handled independently from each other, i.e., each of the components may have at least one state in which the respective component is not mechanically connected to any other component. Further, each of the components of the kit may have an individual function, such as a measurement function, a data storage function and a data transmission function, which may be exerted independently from the presence of other components. The further device may be situated outside the body of the user. For example, the further device may rest on the skin of the user or may be worn by the user. The further device may be adapted to be placed on the skin or an out-of-body surface of the user. Thus, the further device may be an external, extracorporal device. With respect to the definitions and embodiments of the further device, reference is made to definitions and embodiments of the further device described with respect to the first aspect of the disclosure.

The at least one further device may be adapted to provide electrical energy to the rechargeable energy storage device in a contactless fashion, for example via the inductive connection. Other ways of recharging, however, are feasible. The sensor element and the kit may be adapted to provide a concept of recharging on-demand for the rechargeable energy storage device and thus, allowing long-term operation.

The at least one further device may comprise at least one portable data management device. The portable data management device may be adapted to directly or indirectly receive the measurement data and to at least partially display data on at least one display. The term "data management device," as used herein, refers to a device adapted to handle measurement data, such as by storing the measurement data and/or subjecting the measurement data to at least one data evaluation algorithm. Thus, as an example, the data management device may have at least one algorithm for displaying the measurement data, such as by displaying the measurement data on a display device, thereby displaying one or more measurement curves. Additionally or alternatively, averaging algorithms may be applied to the measurement data and/or one or more algorithms adapted to give medical advice to the user. Further, the portable data management device may comprise one or more databases, such as for storing and/or comparing measurement data.

The at least one further device may comprise at least one data reader module adapted to receive measurement data transmitted by the implantable sensor element via wireless communication. The data reader module may comprise at least one data storage device and may be adapted to store the measurement data.

In a further aspect of the present disclosure, a method for determining a concentration of at least one analyte in a body fluid of a user is disclosed. The method comprises the following method steps:
- receiving the sample of body fluid in at least one measurement chamber plate;
- generating at least one illumination light beam in at least one spectral range by using at least one illumination source and transmitting the illumination light beam to the measurement chamber plate;
- at least partially illuminating the measurement chamber plate with the illumination light beam;
- generating at least one reflection light beam in response to the illumination by the illumination light beam;
- at least partially illuminating the sample of body fluid within the measurement chamber plate with the reflection light beam;
- detecting at least one property of the reflection light beam and generating at least one sensor signal dependent on the presence of the analyte by using at least one optical detector; and
- evaluating the sensor signal by using at least one control unit.

The method steps may be performed in the given order or in a different order. Further, one or more or even all of the method steps may be performed once or more than once or even repeatedly. The method may further comprise additional method steps which are not listed. In the evaluation step, at least one information on the analyte may be generated by evaluating the sensor signal.

The method comprises the use of one or both of the sensor element according to the present disclosure, such as according to one or more of the embodiments disclosed above or disclosed in further detail below, and/or of the kit according to the present disclosure, such as according to one or more of the embodiments disclosed above or disclosed in further detail below. For further optional details, reference may be made to the disclosure of the sensor element and/or the kit as given above and/or as given in further detail below.

The sensor element, the kit and the method according to the present disclosure provide a large number of advantages over known devices for detecting at least one analyte in body fluid, such as continuous monitoring glucose sensors. The sensor element is a fully implantable sensor element. The sensor element is based on optical measurements and allows reagent-free analyte monitoring. All components as described above can be miniaturized allowing production of very small sensor elements. The sheet or plate-like geometry ensures mechanical robustness with respect to mechanical influences and thus may ensure signal stability and reliability of measurement data. Further, usage of biocompatible material such as silicon or diamond allows producing an implantable sensor element without additional coatings. Further, using a concept of recharging the rechargeable energy storage device of the sensor element may allow long-term operation of the sensor element. Thus, the sensor element may be embodied as a very small and robust module allowing reagent-free and long-term analyte monitoring.

Summarizing the features of the present disclosure, the following embodiments are preferred. Still, other embodiments are feasible.

Embodiment 1: Fully implantable sensor element for detecting at least one analyte in a sample of body fluid, wherein the fully implantable sensor element comprises at least one measurement chamber plate adapted to receive the sample of bodily fluid, wherein the fully implantable sensor element comprises at least one illumination source designed to generate at least one illumination light beam in at least one spectral range and to transmit the illumination light beam to the measurement chamber plate such that the illumination light beam at least partially illuminates the measurement chamber plate, wherein the measurement chamber plate is designed to generate at least one reflection light beam in response to the illumination by the illumination light beam such that the reflection light beam at least partially illuminates the sample of body fluid within the measurement chamber plate, wherein the fully implantable sensor element comprises at least one optical detector designed to detect at least one property of the reflection light beam and to generate at least one sensor signal dependent on the presence of the analyte, wherein the fully implantable sensor element furthermore comprises at least one control unit designed to evaluate the sensor signal, wherein the illumination source comprises at least one quantum cascade laser, wherein the measurement chamber plate comprises at least one biocompatible polymer membrane having a molecular weight cutoff of at least 15 kDa.

Embodiment 2: Fully implantable sensor element according to the preceding embodiment, wherein the biocompatible polymer membrane has a pore size in a range from 15 to 35 Å.

Embodiment 3: Fully implantable sensor element according to any one of the preceding embodiments, wherein the biocompatible polymer membrane comprises at least one polymer selected from the group consisting of: cellulose hydrate, nitrocellulose, polysulfone, polycarbonate, polyethersulfone, cellulose acetate, polyamide, polytetrafluoroethylene.

Embodiment 4: Fully implantable sensor element according to any one of the preceding embodiments, wherein the biocompatible polymer membrane comprises at least one polymer selected from the group consisting of: cellulose hydrate; nitrocellulose; polysulfone; polyethersulfone; cellulose acetate; polyamide; polytetrafluoroethylene.

Embodiment 5: Fully implantable sensor element according to any one of the two preceding embodiments, wherein the polymer is hydrophilized.

Embodiment 6: Fully implantable sensor element according to any one of the preceding embodiments, wherein the biocompatible polymer membrane has a thickness in a range from 1 to 250 µm, preferably from 20 to 50 µm.

Embodiment 7: Fully implantable sensor element according to any one of the preceding embodiments, wherein the illumination source comprises at least one quantum cascade laser chip.

Embodiment 8: Fully implantable sensor element according to any one of the preceding embodiments, wherein the quantum cascade laser is selected from the group consisting of: at least one fixed-frequency Fabry-Perot quantum cascade laser; at least one tunable external cavity quantum cascade laser; at least one distributed feedback quantum cascade laser.

Embodiment 9: Fully implantable sensor element according to any one of the preceding embodiments, wherein the illumination source is designed to be operated in pulsed or continuous mode.

Embodiment 10: Fully implantable sensor element according to the preceding embodiment, wherein the fully implantable sensor element comprises at least one pulser device adapted to operate the illumination in the pulse mode, wherein the control unit is adapted to control the pulser device.

Embodiment 11: Fully implantable sensor element according to any one of the preceding embodiments, wherein the illumination light beam has a wavelength in the infrared spectral range.

Embodiment 12: Fully implantable sensor element according to the preceding embodiment, wherein the illumination light beam has a wavelength in the mid-infrared spectral range.

Embodiment 13: Fully implantable sensor element according to any one of the preceding embodiments, wherein the illumination source is adapted to change the wavelength continuously over time.

Embodiment 14: Fully implantable sensor element according to any one of the preceding embodiments, wherein the illumination source is adapted to generate a plurality of illumination light beams, wherein each of the illumination light beams has a different wavelength.

Embodiment 15: Fully implantable sensor element according to the preceding embodiment, wherein the control unit is adapted to perform one or more of assign, adjust or select the wavelength of the illumination light beams.

Embodiment 16: Fully implantable sensor element according to the any one of the preceding embodiments, wherein the measurement chamber plate comprises at least one chamber wall, wherein the chamber wall is adapted to receive the sample of body fluid.

Embodiment 17: Fully implantable sensor element according to the preceding embodiment, wherein the measurement chamber plate comprises at least one first chamber wall adapted to be at least partially transparent to the illumination light beam, wherein the first chamber wall is designed as at least one at least partially transparent first infrared window.

Embodiment 18: Fully implantable sensor element according to the preceding embodiment, wherein the first chamber wall comprises at least one anti-reflective coating adapted to minimize reflections from a surface of the first chamber wall to the optical detector.

Embodiment 19: Fully implantable sensor element according to any one of the two preceding embodiments, wherein the measurement chamber plate comprises at least one second chamber wall adapted to at least partially receive the sample of body fluid.

Embodiment 20: Fully implantable sensor element according to the preceding embodiment, wherein the measurement chamber plate comprises at least one capillary element arranged between the first chamber wall and the second chamber wall, wherein the capillary element is adapted to receive the sample of body fluid.

Embodiment 21: Fully implantable sensor element according to any one of the preceding embodiments, wherein the measurement chamber plate comprises at least one spacer element arranged between the first chamber wall and the second chamber wall.

Embodiment 22: Fully implantable sensor element according to any one of the preceding embodiments, wherein the second chamber wall is designed as at least one at least partially reflective second infrared window.

Embodiment 23: Fully implantable sensor element according to the preceding embodiment, wherein the second infrared window comprises at least one reflective layer, wherein the reflective layer is arranged on at least one side of the second infrared window facing the illumination light beam in order to enhance reflection of the illumination light beam.

Embodiment 24: Fully implantable sensor element according to any one of the two preceding embodiments, wherein the second infrared window is designed to permit transport of the analyte into the capillary element.

Embodiment 25: Fully implantable sensor element according to the preceding embodiment, wherein the second infrared window comprises at plurality of holes.

Embodiment 26: Fully implantable sensor element according to any one of the preceding embodiments, wherein the measurement chamber plate comprises at least one attenuated total reflection element.

Embodiment 27: Fully implantable sensor element according to the preceding embodiment, wherein the attenuated total reflection element comprises at least one ATR-crystal, wherein the ATR-crystal is arranged such that the illumination light beam is at least reflected once.

Embodiment 28: Fully implantable sensor element according to the preceding embodiment, wherein the ATR-crystal comprises a structured surface.

Embodiment 29: Fully implantable sensor element according to the preceding embodiment, wherein at least one biocompatible membrane, specifically the biocompatible polymer membrane, is arranged on the ATR-crystal.

Embodiment 30: Fully implantable sensor element according to any one of the preceding embodiments, wherein the sensor element comprises at least one transfer device, wherein the transfer device comprises at least one lens.

Embodiment 31: Fully implantable sensor element according to any one of the preceding embodiments, wherein the optical detector comprises at least one photodetector.

Embodiment 32: Fully implantable sensor element according to the preceding embodiment, wherein the optical detector comprises one or more of at least one pyroelectric detector; at least one Fabry-Perot interferometer.

Embodiment 33: Fully implantable sensor element according to any one of the preceding embodiments, wherein the control unit is adapted for one or more of processing, analyzing, and storing of the sensor signal.

Embodiment 34: Fully implantable sensor element according to any one of the preceding embodiments, wherein the control unit comprises at least one evaluation device designed to evaluate the sensor signal, wherein the evaluation device is designed to generate at least one information on the analyte by evaluating the sensor signal.

Embodiment 35: Fully implantable sensor element according to the preceding embodiment, wherein the evaluation device is adapted to determine at least one spectral information of the reflection light beam from the sensor signal.

Embodiment 36: Fully implantable sensor element according to the preceding embodiment, wherein the evaluation device is adapted to determine from the spectral information the at least one information on the analyte by using uni- or multivariate data analysis, e.g., principle component regression (PCR) and partial least square regression (PLS).

Embodiment 37: Fully implantable sensor element according to any one of the three preceding embodiments, wherein the evaluation device is adapted to perform a temperature correction.

Embodiment 38: Fully implantable sensor element according to the preceding embodiments, wherein the control unit comprises at least one or more of an amplifier circuit adapted to amplify the sensor signal and/or to transform the sensor signal into an electrical current or voltage; at least one analog-/digital converter adapted to digitalize the sensor signal; at least one digital filter adapted to optimize a signal-to-noise ratio such as at least one Lock-In amplifier and/or at least one Boxcar integrator; at least one analog filter adapted to filter the sensor signal; at least one memory unit adapted to store the sensor signal.

Embodiment 39: Fully implantable sensor element according to the any one of the preceding embodiments, wherein the fully implantable sensor element comprises at least one housing adapted to encapsulate further components of the fully implantable sensor element.

Embodiment 40: Fully implantable sensor element according to any one of the preceding embodiments, wherein the fully implantable sensor element comprises at least one rechargeable energy storage device.

Embodiment 41: Fully implantable sensor element according to the preceding embodiment, wherein the rechargeable energy source is adapted to be charged in a contactless fashion.

Embodiment 42: A kit for detecting at least one analyte in a sample of body fluid, the kit comprising at least one fully implantable sensor element according to any one of the preceding embodiments, and at least one further device, wherein the further device is adapted to provide energy to at least one rechargeable energy storage device.

Embodiment 43: The kit according to the preceding embodiment, wherein the at least one further device is adapted to provide electrical energy to the rechargeable energy storage device in a contactless fashion.

Embodiment 44: The kit according to any one of the preceding embodiments referring to a kit, wherein the at least one further device comprises at least one data reader module adapted to receive measurement data transmitted by the fully implantable sensor element via wireless communication, wherein the data reader module comprises at least one data storage device and is adapted to store the measurement data.

Embodiment 45: Method for detecting at least one analyte in a sample of body fluid comprising the following method steps:
receiving the sample of body fluid in at least one measurement chamber plate;
generating at least one illumination light beam in at least one spectral range by using at least one illumination source and transmitting the illumination light beam to the measurement chamber plate;
at least partially illuminating the measurement chamber plate with the illumination light beam;
generating at least one reflection light beam in response to the illumination by the illumination light beam;
at least partially illuminating the sample of body fluid within the measurement chamber plate with the reflection light beam;
detecting at least one property of the reflection light beam and generating at least one sensor signal dependent on the presence of the analyte by using at least one optical detector; and
evaluating the sensor signal by using at least one control unit, wherein the method comprises a use of one or both of at least one fully implantable sensor element according to any one of the preceding embodiments referring to a fully implantable sensor element or a kit according to any one of the preceding embodiments referring to a kit.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
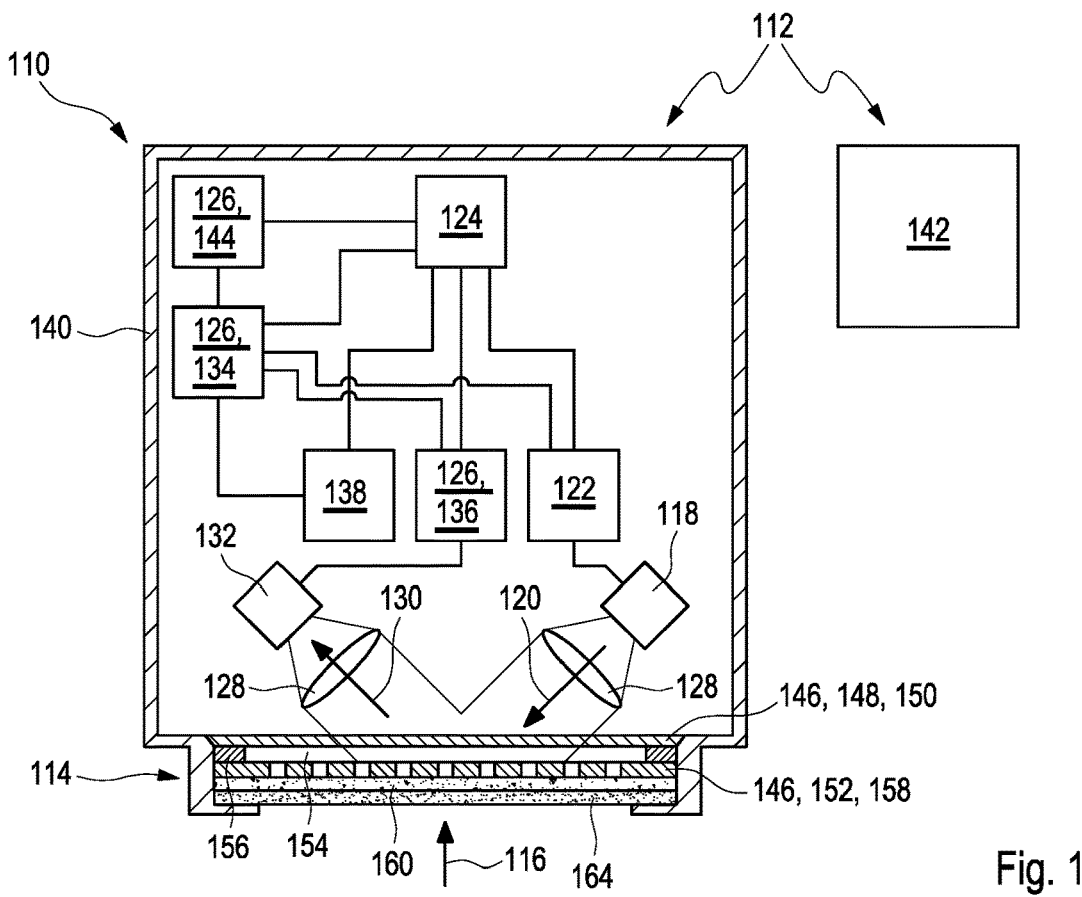
FIG. 1 shows an exemplary embodiment of an implantable sensor element and kit according to the present disclosure.

In FIG. 1, an exemplary embodiment of a fully implantable sensor element (also referred to herein as "sensor") 110 and a kit 112 for detecting at least one analyte in a body fluid is disclosed. The sensor element 110 may be designed to remain in the body tissue for an elongated time period, such as for several days or even several weeks or several months. The sensor element 110 is embodied as a fully implantable transcutaneous sensor element. Generally, an arbitrary type of body fluid may be used. Preferably, the body fluid is a body fluid which is present in a body tissue of the user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue. Thus, generally, the detection of the at least one analyte in the body fluid may preferably be determined in vivo.

The sensor element 110 comprises at least one measurement chamber plate (also referred to herein as "chamber plate") 114 adapted to receive the sample of bodily fluid. The measurement chamber plate 114 may have a sheet or plate-like geometry. The measurement chamber plate 114 may have a flat geometry. The measurement chamber plate 114 may comprise a monolithic or a multi-plate setup. The measurement chamber plate 114 may receive the sample of body fluid via diffusion processes. In FIG. 1, a direction of diffusion of the body fluid is denoted with arrow 116. Filling the sample via diffusion processes may ensure maintenance-free operation of the implanted sensor element.

The sensor element 110 comprises at least one illumination source 118 designed to generate at least one illumination light beam 120 in at least one spectral range and to transmit the illumination light beam 120 to the measurement chamber plate 114 such that the illumination light beam 120 at least partially illuminates the measurement chamber plate 114.

The illumination source 118 may comprise at least one light source. The illumination source 118 comprises at least one quantum cascade laser. For example, the illumination source 118 may comprise at least one quantum cascade laser chip. The quantum cascade laser may be a miniaturized quantum cascade laser. The quantum cascade laser may be selected from the group consisting of: at least one fixed-frequency Fabry-Perot quantum cascade laser; at least one tunable external cavity quantum cascade laser; at least one distributed feedback quantum cascade laser. For example, the illumination source 118 may comprise at least one array of quantum cascade lasers. The illumination source 118 may be designed to be operated in pulsed or continuous mode. The sensor element 110 may comprise at least one pulser device 122 adapted to operate the illumination in the pulsed mode. The sensor element 110 may comprise at least one rechargeable energy storage device 124, for example at least one lithium-ion battery, adapted to supply energy to the quantum cascade laser. The quantum cascade laser may have a low power consumption such that power supply by lithium-ion battery, is possible.

The illumination light beam 120 may have a wavelength in the infrared spectral range, preferably in mid-infrared spectral range. The illumination source 118 may be adapted to generate broadband illumination light or illumination light having a narrow bandwidth. The illumination source 118 may be adapted to change the wavelength continuously over time. The illumination source 118 may be adapted to generate a plurality of illumination light beams 120, wherein each of the illumination light beams has a different wavelength. The sensor element comprises at least one control unit (also referred to herein as "controller") 126. The control unit 126 may be adapted to one or more of assign, adjust or select the wavelength of the illumination light beams. For example, the illumination source 118 may comprise at least one tunable distributed feedback quantum cascade laser and/or at least one tunable external cavity quantum cascade laser having a narrow bandwidth. The control unit 126 may be adapted to change the wavelength continuously or non-continuously, for example within the mid-infrared spectral range. The control unit 126 may be adapted to adjust and/or select wavelengths suitable for identification of glucose and/or distinction of glucose from further substances in the sample of body fluid, for example substances present even after filtration such as maltose. Additionally or alternatively, a broadband spectral range is used. For example, the illumination source 118 may comprise at least one Fabry-Perot quantum cascade laser. In order to permit absorption measurements with a broadband illumination source, the sensor element 110 may comprise several optical detectors and suitable spectral bandpass filters or at least one tunable optical detector having at least one tunable, spectral bandpass filter.

The illumination light beam 120 may illuminate more than 5% of the measurement chamber plate 114, preferably more than 10% of the measurement chamber plate 114, more preferably more than 25% of the measurement chamber plate 114. However, embodiments are feasible. The illumination light beam 120 may illuminate the measurement chamber plate 114 under an illumination angle between 0° and 85°, preferably between 20° and 60°, more preferably between 30° and 50°. For example, the illumination angle may be 45°.

The sensor element 110 may comprise at least one transfer device 128 adapted to collimate the illumination light beam 120. The transfer device 128 may comprise at least one optical lens, such as one or more convex lenses, one or more refractive lenses. For example, the transfer device 128 may be arranged such that the illumination light beam 120 travels first through the at least one transfer device 128 and thereafter to the measurement chamber plate 114.

The measurement chamber plate 114 is designed to generate at least one reflection light beam 130 in response to the illumination by the illumination light beam 120 such that the reflection light beam 130 at least partially illuminates the sample of body fluid within the measurement chamber plate 114. Preferably, the sample of body fluid is illuminated by the illumination light beam 120 before the sample of body fluid is illuminated by the reflection light beam 130. Preferably, the sample of body fluid may be illuminated at least twice within the measurement chamber plate 114. The sample may be illuminated, firstly, by the illumination light beam 120, for example in a first direction, and, subsequently, by the reflection light beam 130, for example, in a second direction. The measurement chamber plate 114 may comprise at least one reflector element and/or may comprise a reflective material such as a reflective coating. The measurement chamber plate 114 may be adapted to at least partially reflect the illumination light beam 120.

The sensor element 110 comprises at least one optical detector 132 designed to detect at least one property of the reflection light beam 130 and to generate at least one sensor signal dependent on the presence of the analyte. The sensor signal may be or may comprise a digital and/or an analog signal. The sensor signal may be or may comprise a voltage signal and/or a current signal. Additionally or alternatively, the sensor signal may be or may comprise digital data. The sensor signal may comprise a single signal value and/or a series of signal values. The sensor signal may further comprise an arbitrary signal which is derived by combining two or more individual signals, such as by averaging two or more signals and/or by forming a quotient of two or more signals. The optical detector 132 may comprise at least one photodetector. The optical detector 132 may comprise at least one pyroelectric detector. The optical detector 132 may comprise at least one spectrometric setting, for example at least one Fabry-Perot interferometer. The optical detector 132 may comprise at least one analog and/or digital amplifier and/or filter in order to for example amplify at least one property of the reflection light beam 130 and/or reduce noise. The optical detector 132 may be adapted to determine one or more of intensity, absorbance, attenuation, transmission, reflection, wavelength and frequency of the reflection light beam 130. The at least one property of the reflection light beam 120, for example the intensity, may change due to the presence of the analyte and/or other substances in the sample of body fluid. The optical detector 132 may be adapted to determine a change in intensity, for example due to the presence of the analyte and/or other substances in the sample of body fluid. The sensor element 110 may be adapted to perform one or more of at least one reflection measurement, at least one absorption measurement, at least one attenuated total reflectance measurement. The optical detector 132 may be adapted to determine at least one absorption information and/or attenuation information as a function of wavelength and/or frequency of the reflection light beam 130. The optical detector 132 may be adapted to determine at least one spectrum, for example at least one absorbance spectrum, of the reflection light beam. The sensor element 110 may comprise at least one further transfer 128 which may be arranged such that the reflected light beam travels from the measurement chamber plate 114 to the further transfer device 128 until it may finally impinge on the optical detector 132.

The sensor element furthermore comprises the at least one control unit 126 designed to evaluate the sensor signal. The control unit 126 may be adapted for one or more of processing, analyzing, and storing of the sensor signal. The control unit 126 may be a central control unit. The control unit 126 may comprise at least one evaluation device 134 designed to evaluate the sensor signal. The evaluation device 134 may be designed to generate at least one information on the analyte by evaluating the sensor signal. As an example, the evaluation device 134 may be or may comprise one or more integrated circuits, such as one or more application-specific integrated circuits (ASICs), and/or one or more data processing devices (also referred to herein as "data processors"), such as one or more computers, preferably one or more microcomputers and/or microcontrollers. Additional components may be comprised, such as one or more pre-processing devices and/or data acquisition devices, such as one or more devices for receiving and/or preprocessing of the sensor signals, such as one or more AD-converters and/or one or more filters. Further, the evaluation device 134 may comprise one or more data storage devices. Further, the evaluation device 134 may comprise one or more interfaces, such as one or more wireless interfaces and/or one or more wire-bound interfaces. The evaluation device 134 may be adapted to determine at least one spectral information of the reflection light beam from the sensor signal. The spectral information may be at least one absorption spectrum or at least one attenuation spectrum. For example, spectra may be acquired by continuously changing the laser's wavelength over time and measuring the sensor signal on the optical detector. The difference in absorbance $\Delta A$ can be calculated using water as a reference, Iref, by $$\Delta A = -\log[(I_{meas})/(I_{ref})],$$

with $I_{meas}$ being the sensor signal seen.

The evaluation device 134 may be adapted to determine the analyte concentration by evaluating the spectral information. The evaluation device 134 may be designed to identify characteristic spectral signature of molecules in the mid-infrared spectral range. The evaluation device 134 may be adapted to compare the measured spectral information with predetermined or theoretical spectral information stored, for example, in an electronic table such as in at least one look-up table. The evaluation device 134 may be adapted to determine from the spectral information the at least one information on the analyte by using uni- or multivariate data analysis, e.g., principle component regression (PCR) and partial least square regression (PLS). The evaluation device 134 may be adapted to detect and potentially quantify a variety of biomolecules using uni- or multivariate data analysis. For example, the evaluation device 134 may be adapted to determine the presence and/or concentration of glucose. The evaluation device 134 may be adapted to identify and/or determine a relevant signal or signal component, for example a signal referring to glucose, and to distinguish the relevant signal from signals of interfering molecules. The evaluation device 134 may be adapted to distinguish the relevant signal from other signal influences such as from signal influences due to system changes such as temperature.

The control unit 126 may comprise at least one or more of amplifier circuits 136 adapted to amplify the sensor signal and/or to transform the sensor signal into an electrical current or voltage; at least one analog-/digital converter adapted to digitalized the sensor signal, for example the amplified sensor signal; at least one digital filter adapted to optimize a signal-to-noise ratio such as at least one Lock-In amplifier and/or at least one Boxcar integrator; at least one analog filter adapted to filter the sensor signal, for example before digitalization; at least one memory unit (also referred to herein as "memory") 138 adapted to store the sensor signal, for example the raw sensor signal and/or the evaluated, for example digitalized and/or amplified, sensor signal. The memory unit 138 generally may comprise at least one data storage device such as at least one volatile and/or at least one non-volatile data storage element. The components listed above may be designed as separate components within a housing 140 of the sensor element 110. Alternatively, two or more of the components as listed above may be integrated into one component. For example, the optical detector 132 may comprise an integrated amplifier circuit and/or one or more signal filters. Additionally or alternatively, one or more of these components may be provided in a further device 142 of the kit 112 situated outside the body of the user. The sensor element 110 can be adapted to transfer data, such as the raw sensor signal and/or the evaluated sensor signal, automatically and/or upon request to the further device 142 for evaluation and data storing. The control unit 126 can be designed to receive instructions and/or data, for example from the further device 142, contactless, for example via the inductive connection. The sensor element and the further device may be adapted to communicate, i.e., transfer data and instructions, wirelessly such as by an inductive connection. Other ways of data transfer, however, are feasible. The control unit 126 may comprise at least one communication unit 144 for wireless communication. Read-out of the measurement data from the sensor element 110 may be performed wireless such that wearing comfort and freedom of movement is enhanced.

The evaluation device 134 may be adapted to perform a temperature correction. The sensor signal may be influenced due to temperature changes such that drifts in signal may occur. The evaluation device 134 may be adapted to distinguish signal drift due to temperature change from signal drift due to changes in analyte concentration by using spectral information. The temperature influence may be corrected using calibration data from a prior temperature calibration measurement. Additionally or alternatively, the sensor element 110 may comprise at least one temperature sensor as for example a platinum resistance thermometer. The temperature sensor may be arranged in close proximity to the measurement chamber plate 114. The temperature influence may be corrected using calibration data from a prior temperature calibration measurement and the measured temperature of the temperature sensor.

Figure 2:
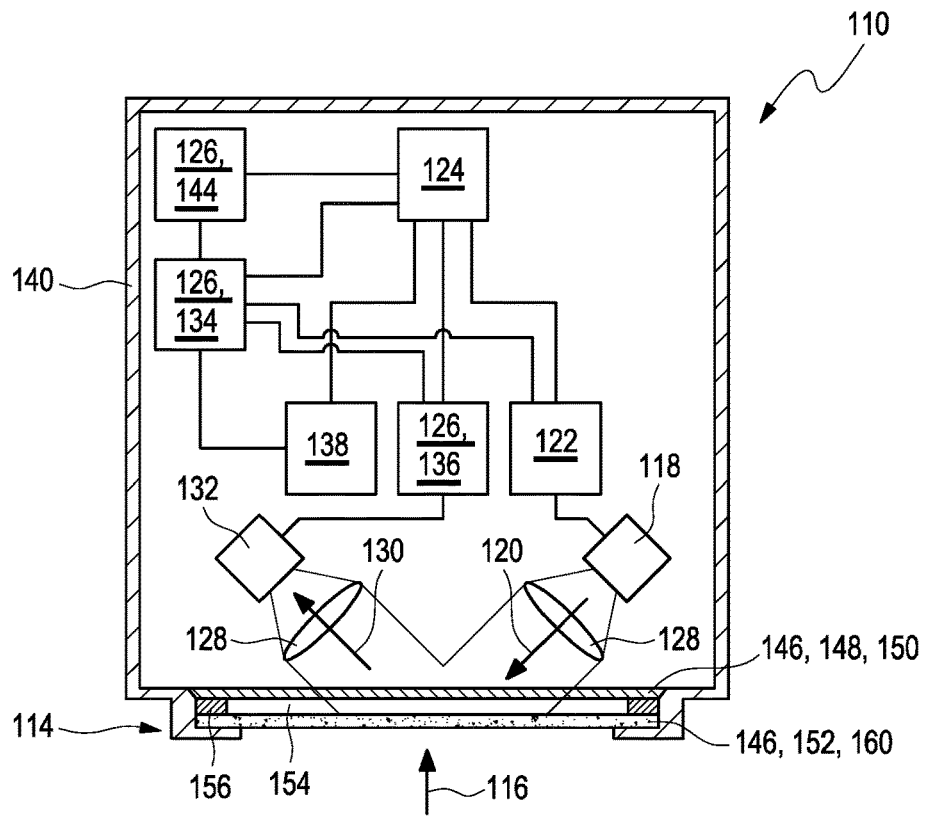
FIG. 2 shows a further exemplary embodiment of the implantable sensor element.

In the embodiments shown in FIGS. 1 and 2, the measurement chamber plate 114 may comprise at least one chamber wall 146, wherein the chamber wall 146 is adapted to receive the sample of body fluid. The sensor element 110 may be adapted to perform at least one measurement based on absorption spectroscopic techniques using a miniaturized fluid cell. The measurement chamber plate 114 may be adapted to receive a sample size of body fluid such that a reliable absorption measurement can be performed. For example, a layer thickness of body fluid in the measurement chamber plate 114 may be between 1 µm and 100 µm, preferably between 5 µm and 50 µm, more preferably the layer thickness may be between 8 µm and 15 µm. For example, the layer thickness may be 10 µm in order to ensure high sensitivity to detect glucose in aqueous solution. The chamber wall 146 may be adapted to have a first side at least partially permeable to light, for example in the infrared spectral range, and a second side at least partially permeable to the sample of body fluid. The first side of the chamber wall 146 may be at least partially transparent. The chamber wall 146 may be arranged such that the side permeable to the sample of body fluid faces an exterior of the sensor element 110.

In the embodiments depicted in FIGS. 1 and 2, the measurement chamber plate 114 may comprise at least one first chamber wall 148 adapted to be at least partially transparent to the illumination light beam 120. The first chamber wall 148 may be impermeable for fluids. The first chamber wall 148 may be designed as at least one at least partially transparent first infrared window 150. The first chamber wall 148 may be arranged facing an interior of the sensor element 110 such as an interior surrounded by the housing 140. The first chamber wall 148 may face the illumination light beam 120. The first infrared window 150 may be designed to let at least partially the illumination light beam 120 through the infrared window 150 to the sample of body fluid. For example, the infrared window 150 may be designed to let at least partially the illumination light beam pass 120 through the infrared window 150 into the measurement chamber plate 114. The first chamber wall 148 may be designed as transmission window. The first chamber wall 148 may be a light-permeable inner plate. The first chamber wall 148 may be biocompatible. The first chamber wall 148 may comprise and/or may be produced from at least one biocompatible material. The first chamber wall 148 may consist fully of biocompatible material, for example a biocompatible material comprising at least one synthetic diamond or silicon. The first chamber wall 148 may comprise at least one anti-reflective coating adapted to minimize reflections from a surface of the first chamber wall 148 to the optical detector 132 and/or reflections of the reflected beam back into the measurement chamber plate 114, for example in order to minimize interference effects on the signal. The first chamber wall 148 may comprise at least one microstructured surface, e.g., roughened surface adapted to minimize reflections from a surface of the first chamber wall to the optical detector and/or reflections of the reflected beam back into the measurement chamber plate 114 for example in order to minimize interference effects on the signal.

The measurement chamber plate 114 may comprise at least one second chamber wall 152 adapted to at least partially receive the sample of body fluid. The second chamber wall 152 may be a fluid-permeable outer plate. The measurement chamber plate 114 may comprise at least one capillary element 154 arranged between the first chamber wall 148 and the second chamber wall 152. The capillary element 154 may be adapted to receive the sample of body fluid. The receiving of the sample of body fluid may be supported by capillary forces. The first chamber wall 148 and the second chamber wall 152 may be arranged at opposing sides of a capillary element 154 and form a measurement cuvette. The capillary element 154 may be designed to receive an amount of body fluid required for reliable determination of the analyte. In order to obtain a maximum sensitivity of glucose in aqueous solution, the capillary element may be designed to receive a fluid layer thickness between 1 to 100 µm, preferably between 5 and 50 µm, more preferably between 8 and 15 µm. For example, the capillary element 154 may be designed to receive a fluid layer thickness of 10 µm. Generally, the thickness of the measurement chamber plate 114 is composed of the thickness of the individual components of the measurement chamber plate 114. The thickness of the measurement chamber plate 114 may be composed for example of the thickness of the windows, membranes and fluidic layer (1 to 80 µm). The capillary element 154 may receive the sample of body fluid via diffusion processes. In order to ensure suitable sensor response behavior, the capillary element 154 may be designed such that diffusion distances are as short as possible, preferably around 100 µm.

The measurement chamber plate 114 may comprise at least one spacer element 156 arranged between the first chamber wall 148 and the second chamber wall 152. The spacer element 156 may have an arbitrary shape, for example the spacer element may be at least one ring. The spacer element may have a thickness between 1 and 100 µm. The spacer element 156 may be a cut polyester film. Additionally or alternatively, one of the first chamber wall 148 and the second chamber wall 152 may comprise at least one cavity and/or recess, for example produced by photolithographic methods, adapted to form a capillary element 154.

The second chamber wall 152 may be designed to be rigid against mechanical influence, for example, during assembling of the sensor element 110, such that a constant measurement volume can be ensured. The second chamber wall 152 may be designed to be permeable to the analyte, for example, to glucose, such that the analyte can reach the measurement chamber plate. The second chamber wall 152 may be designed to prevent large-sized molecules and/or cells to penetrate into the measurement chamber plate 114.

In FIG. 1, the second chamber wall 152 may be designed as at least one at least partially reflective second infrared window 158. The second infrared window may 158 comprise at least one reflective layer, for example a gold layer. The reflective layer may be arranged on at least one side of the second infrared window 158 facing the illumination light beam 120 in order to enhance reflection of the illumination light beam 120. The second infrared window 158 may be designed to permit transport, for example by diffusion, of the analyte into the capillary element 154. The second infrared window 158 may be a fluid-permeable outer plate. The second infrared window 158 may comprise a plurality of holes. The second infrared window 158 may comprise a plurality of micro fluid channels. For example, the holes may be drilled micro holes having a diameter less than 100 µm, preferably less than 20 µm, more preferably less than 10 µm. An average distance between two holes may be less than 500 µm, preferably less than 200 µm, more preferably less than 100 µm. A thickness of the second infrared window 158 may be from 50 to 1000 µm, preferably from 50 to 500 µm, most preferably from 50 to 300 µm. Such dimensions may ensure short diffusion times of glucose from interstitial fluid into the capillary element. The holes may have other shapes as for example slits or bendings. The holes may be produced using laser processing techniques or other methods known in the art, for example wet etching. The second infrared window 158 may be or may comprise a silicon plate having a plurality of holes. Such a design can ensure proper rigidity. The silicon plate may be sputtered with a gold layer in order to enhance reflectivity. The second chamber wall 152 may have a hydrophilic surface structure on one side and/or on the other side and/or in the holes of the wall adapted to have better fluidic properties. This hydrophilic surface may be made by a microfabricated surface for example by photolithographic or wet etching methods.

The measurement chamber plate 114 comprises at least one biocompatible polymer membrane 160 having a molecular weight cutoff of at least 15 kDa. The biocompatible polymer membrane 160 may be adapted to protect the measurement chamber plate 114 from penetration of particles above a certain size such as large-sized molecules like proteins. In the embodiment of FIG. 1, the measurement chamber plate may comprise a flat biocompatible polymer membrane 160. The flat plate design of the measurement chamber plate 114 may allow simple mounting of the flat biocompatible polymer membrane 160. In case of using the flat biocompatible polymer membrane 160, the diffusion distance may be enhanced only slightly by the thickness of the flat membrane. The biocompatible polymer membrane 160 may be arranged on the side of the second infrared window 158. The biocompatible polymer membrane 160 may be arranged on an outer side of the second chamber wall 152. The biocompatible polymer membrane 160 and the second chamber wall 152 may be designed as separate elements. The biocompatible polymer membrane 160 may be non-flexible. The biocompatible polymer membrane 160 may be configured as a rigid element. Specifically, the biocompatible polymer membrane 160 is not one or more of toxic, injurious, or physiologically reactive and/or does not cause immunological rejections. The biocompatible polymer membrane 160 may comprise at least one polymer selected from the group consisting of: cellulose hydrate; nitrocellulose; polysulfone; polycarbonate, preferably a capillary pore membrane; polyethersulfone; cellulose acetate; polyamide; polytetrafluoroethylene. The polymer may be hydrophilized. Cellulose hydrate is also known as regenerated cellulose to the skilled person. Thus, the biocompatible polymer membrane 160 may be and/or may comprise regenerated cellulose. Polysulfone may be obtainable by polymerization of Bisphenol A and 4,4'-Dichlorodiphenyl sulfone. Polyethersulfone may be obtainable by polymerization of 4,4'-Dichlorodiphenyl sulfone and 4,4'-Dihydroxydiphenyl sulfone. Polyamide is also known as Nylon. The polyamide may be selected from the group consisting of polyamide 6, polyamide 6,6, polyamide 6,12 and polyamide 12. The biocompatible polymer membrane 160 may have a pore size in a range from 15 to 35 Å. The biocompatible polymer membrane 160 may have a thickness in a range from 1 to 250 µm, preferably from 20 to 50 µm. For example, in case of a regenerated cellulose the thickness may be from 20 to 250 µm. The biocompatible polymer membrane 160 may be configured for preventing ingress of macromolecules and cells into the measurement chamber 154. The biocompatible polymer membrane 160 may prevent blocking of the measurement chamber 154 due to ingress of macromolecules and cells. The biocompatible polymer membrane 160 may prevent damages of the measurement chamber 154 due to ingress of macromolecules and cells. The biocompatible polymer membrane 160 may be configured for reducing influence from proteins on the absorption measurement. Usage of the biocompatible polymer membrane 160 may allow stable reflectivity and a thickness of the absorption layer over a long period of time and thus, stable glucose sensitivity. Additionally, to the biocompatible polymer membrane 160, the holes of the second infrared window 158 may be designed such that the second infrared window 158 functions as membrane. Additionally, specifically in order to achieve biocompatibility and/or to provide the membrane with required hydrophilic properties, the biocompatible polymer membrane 160 may have a coating 164 on an outer side of the biocompatible polymer membrane 160, specifically on the side facing the tissue or body fluid.

The sensor element 110 may comprise the at least one housing 140 adapted to encapsulate the further components of the sensor element 110 such as the illumination source 118, the control unit 126 and the optical detector 132. The housing 140 may allow complete or at least partial implantation of the sensor element 110 within the body of the user. Thus, the housing 140 may prevent permanent open skin barrier and thus, the housing 140 may prevent penetration of bacteria and other contaminations in the body. The housing 140 may be designed to prevent contamination of the sensor element, for example with dirt and moisture. The housing 140 may be biocompatible in order to reduce and/or minimize specific immune reactions. The housing 140 may comprise and/or is produced from biocompatible material. For example, the biocompatible material may comprise titanium alloy.

The sensor element 110 may comprise the at least one rechargeable energy storage device 124. The rechargeable energy storage device 124 may be adapted to supply voltage for one or more of the sensor element 110 such as to illumination source 118, the control unit 126, in particular the amplifier circuit, and the optical detector 132, pulser device 122 etc. The control unit 126 may be adapted to control power supply to the components of the sensor element 110. For example, the control unit 126 may be adapted to control power supply to one or more of the optical detector 132 such as to the amplifier circuit, the illumination source 118 such as the pulser device 122. The rechargeable energy source 124 may be adapted to be charged in a contactless fashion. For example, the rechargeable energy storage device 124 may be adapted to be charged wirelessly such as by an inductive connection. Other ways of recharging, however, are feasible. Charging in a contactless fashion may allow long-term operation without surgical interventions. The rechargeable energy storage device 124 may comprise at least one lithium-ion battery. The rechargeable energy storage device 124 may be charged by using the further device situated outside the body of the user such as by using a docking station or the like. For example, the further device 142 may be designed to be worn by the user. The further device 142 may comprise at least one further rechargeable energy storage device. The further rechargeable energy storage device may be adapted to be charged using at least one cable. The further device 142 may be adapted to bring a demand for recharging the rechargeable energy storage device 124 to a user's attention, such as in one or more of a visual fashion, an acoustic fashion or a vibrational fashion. Thus, as an example, the further device 142 may be adapted to provide at least one of a visual indication, such as a display of an appropriate message, and/or an acoustic indication, such as a warning sound or a voice message, and/or a vibrational indication, such as a vibrational alarm, to a user, in order to indicate to the user that a recharging of the rechargeable energy storage device 124 is required.

As shown in FIG. 1, the kit 112 comprises the at least one implantable sensor element 110 and the at least one further device 142. The further device 142 may be situated outside the body of the user, for example the further device 142 may rest on the skin of the user or may be worn by the user. The further device 142 may be adapted to be placed on the skin or an out-of-body surface of the user. Thus, the further device 142 may be an external, extracorporal device. As outlined above, the further device 142 is adapted to provide energy to at least one rechargeable energy storage device 124. The at least one further device 142 may be adapted to provide electrical energy to the rechargeable energy storage device 124 in a contactless fashion, for example via the inductive connection. Other ways of recharging, however, are feasible. The sensor element 110 and the kit 112 may be adapted to provide a concept of recharging on-demand for the rechargeable energy storage device and thus, allowing long-term operation.

In the embodiment shown in FIG. 2, the second chamber wall 152 may be designed as membrane element 160. With respect to further elements of the sensor element 110 shown in FIG. 2, reference is made to the description of FIG. 1 above. The second chamber wall 152 may have reflective properties. For example, the second chamber wall 152 may comprise at least one sintered metal. The second chamber wall 152 may be sputtered with a reflective layer such as a gold, silver or aluminum layer to enhance reflectivity. For example, the second chamber wall 152 may be selected from the group consisting of a track-etched membrane comprising polycarbonate; an Anodisc membrane comprising aluminum oxide; a membrane having a supporting structure such as a polymeric microporous membrane available from Precision Membranes, LLC; a high-aspect-ratio membrane comprising silicon and/or carbon available from Precision Membranes, LLC; a porous membrane comprising sintered metal. In one embodiment, the second chamber wall 152 may be a membrane having a supporting structure such as a polymeric microporous membrane available from Precision Membranes, LLC. The supporting structure may be adapted to provide rigidity to the measurement chamber plate. The second chamber wall 152 having the supporting structure may have a thickness of several 10 µm such that the membrane element can be used as spacer element 156. In a further embodiment, the second chamber wall 152 may be a high-aspect-ratio membrane comprising silicon and/or carbon available from Precision Membranes, LLC. The high-aspect-ratio membrane may have a reflective coating, for example, the membrane element may be sputtered with a gold layer. However, embodiments are feasible, without a reflective coating, e.g., a porous membrane comprising sintered metal has reflective properties in the infrared spectral range.

Figure 3:
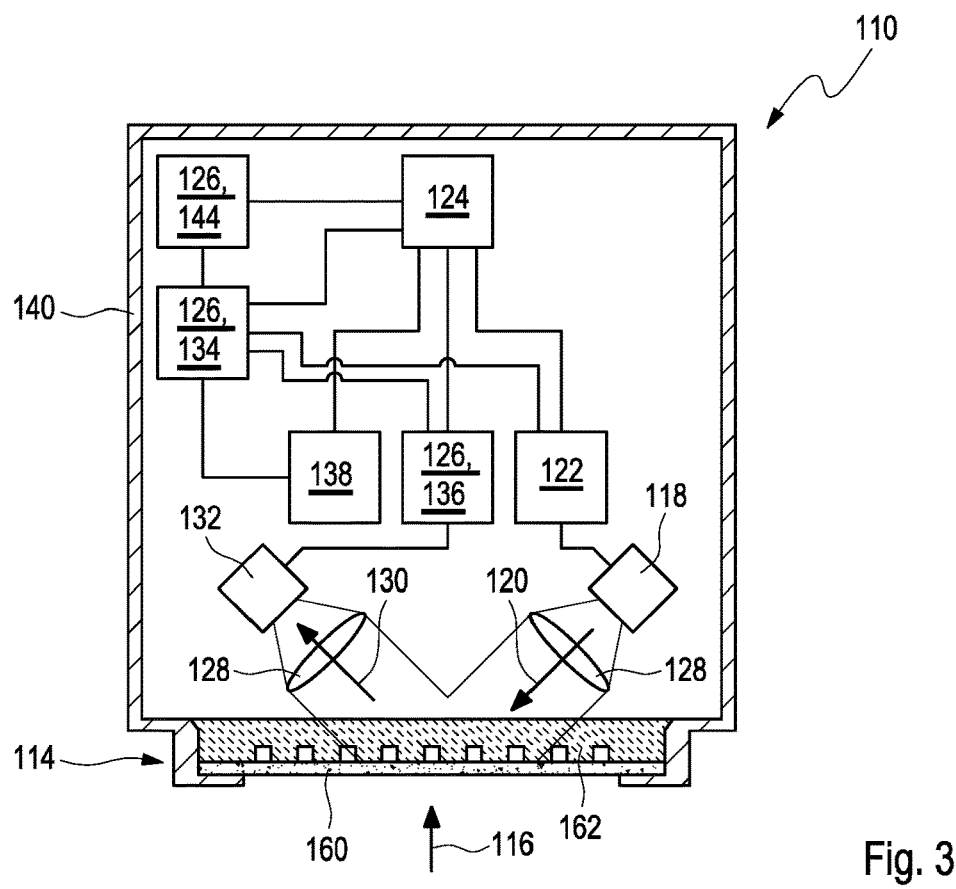
FIG. 3 shows a further exemplary embodiment of the implantable sensor element.

In the embodiments shown in FIG. 3, the measurement chamber plate 114 may comprise at least one attenuated total reflection element 162. With respect to further elements of the sensor element 110 shown in FIG. 3, reference is made to the description of FIGS. 1 and 2. The attenuated total reflection element 162 may comprise at least one ATR-crystal, for example an ATR-crystal available from IRUBIS. The ATR-crystal may comprise a structured surface. The ATR-crystal may comprise at least one microstructure adapted to receive the sample of body fluid. The microstructure may enhance amplification of the sensor signal compared to ATR-crystals without microstructures. The microstructure may be adapted as capillary, wherein the receiving of the sample of body fluid may be supported by capillary forces. The microstructure may have hydrophilic properties such that the microstructure is adapted to draw out the body fluid when in contact with the interstitial fluid. Thereby a transition layer may be formed having a fixed thickness in which the reflection measurement can be performed. The ATR-crystal may be arranged such that the illumination light beam 120 is at least reflected once. Preferably, the illumination light beam 120 may be reflected several times within the ATR-crystal. The illumination light beam 120 may be collimated by the at least one transfer device 128, and may impinge on the ATR-crystal. The ATR-crystal may be designed such that the illumination light beam 120 is reflected by an area of the ATR-crystal comprising the body fluid. The ATR-crystal may be biocompatible. The ATR-crystal may comprise or may be produced from biocompatible material, for example silicon or diamond. The ATR-crystal may be adapted to reflect the light beam such that it illuminates the optical detector 132, for example after being collimated by at least one further transfer device 128. In FIG. 3 an embodiment is shown wherein the at least one biocompatible polymer membrane 160 may be arranged on the ATR-crystal.

Figure 4:
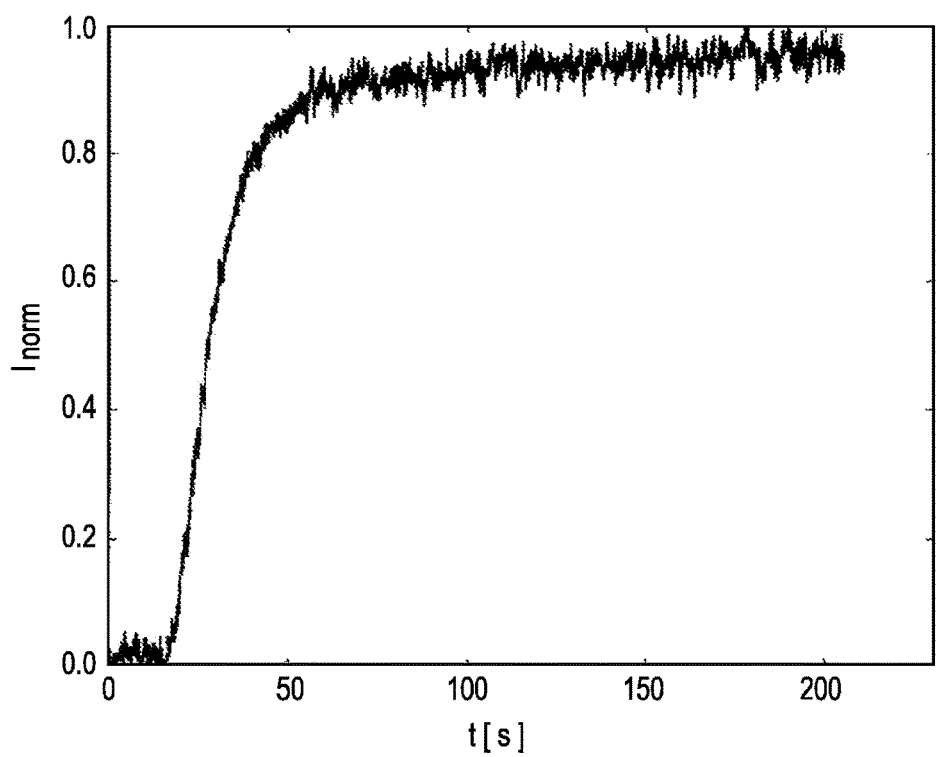
FIG. 4 shows experimental results of a diffusion measurement without using a biocompatible polymer membrane according to the present disclosure.

FIG. 4 shows a typical glucose concentration progress in the measurement chamber 154 during a diffusion process using a sensor element 110 without the biocompatible polymer membrane 160. In the experiment, the diffusion through the second chamber wall 142 was measured by changing the surrounding concentration of glucose from 0 to 500 mg/dL and measuring the optical response on the diffusion. The reservoir surrounding the sensor element 110 was filled with a pumprate of 30 cycles per minute, corresponding to a volume of 7.8 mL/min. For the experiments shown in FIGS. 4 to 8, the quantum cascade laser was set to a fixed wavenumber of 1045 cm-1 for glucose solutions and maltodextrin solutions and 1548 cm-1 for albumin solutions and a transflection signal was measured simultaneously to pumping into the reservoir.

FIG. 4 shows the normalized transflection signal Inorm as a function of time t in seconds. FIG. 4 shows that after around 50 s equilibrium is reached. Using Fick's law the diffusion process can be assumed to have an exponential behavior: $C_{inside}=C_{outside}(1-\exp(-t/\tau))$, wherein $\tau$ indicates the time at which the inner concentration reached $1-1/e$ of the outer concentration. This function can be used for a regression on the acquired curve in order to derive the respective diffusion times $\tau$ for different experimental setups.

Figure 5:
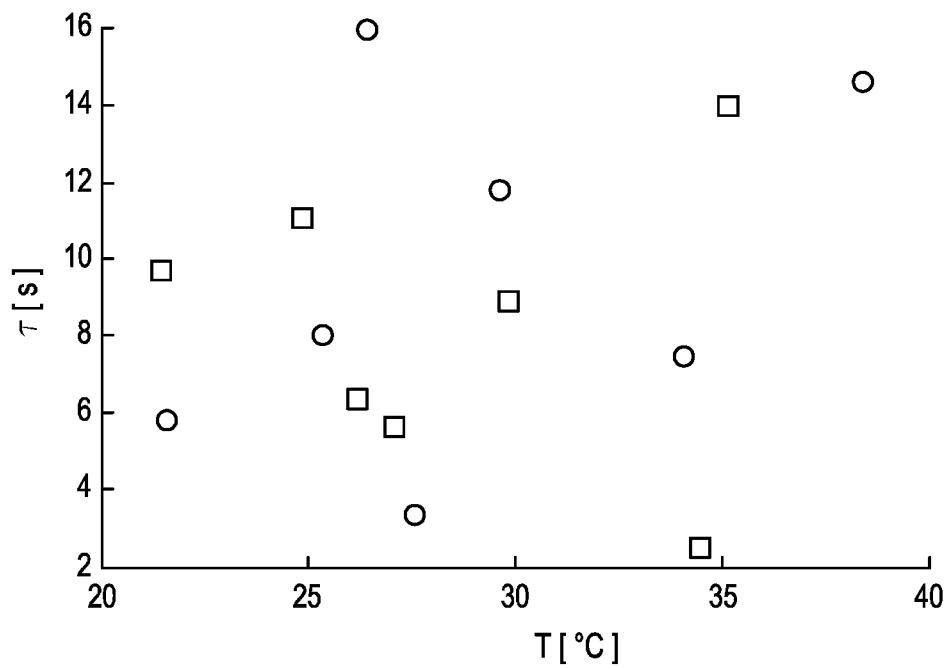
FIG. 5 shows experimental results of dependence of diffusion time of glucose on temperature without using the biocompatible polymer membrane according to the present disclosure.

For example, FIG. 5 shows, for the same experimental setup, i.e., without using the biocompatible polymer membrane 160, experimental results of dependency of diffusion time $\tau$ in seconds on temperature T in ° C. The squares indicated measurements where glucose diffusion direction was out of the chamber, whereas the circles indicate measurements glucose diffusing into the chamber. No dependency of diffusion time on temperature was observed.

Figure 6:
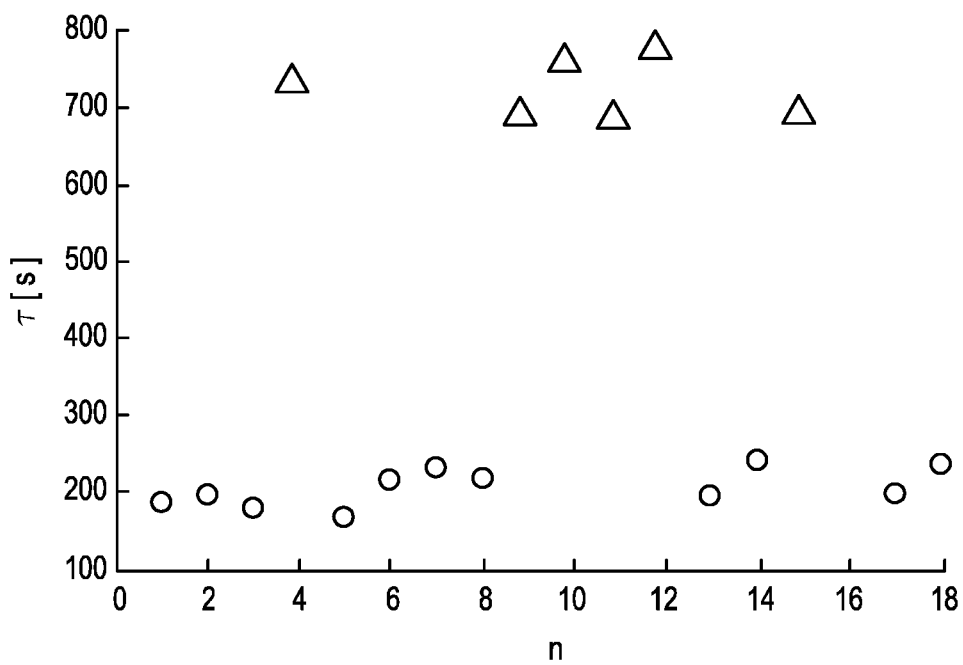
FIG. 6 shows experimental results of acquired diffusion times of the sensor element with the biocompatible polymer membrane for glucose and maltodextrin at room temperature.

FIG. 6 shows experimental results of acquired diffusion times $\tau$ in seconds of the sensor element 110 with the biocompatible polymer membrane 160 for glucose and maltodextrin solutions at room temperature as a function of the measurement order n. In this experimental setup the sensor element 110 comprises as biocompatible polymer membrane 160 a regenerated cellulose membrane with a nominal weight cutoff of 25 kDa available under Nr. 15004, Reichelt Chemietechnik. The diffusion time was measured at room temperature for glucose solution indicated by triangles and for maltodextrin solution indicated as circles. For glucose, a diffusion time around 200 s is acquired and for maltodextrin a diffusion time in the range of 950 s is acquired. This measurement shows a present filtering effect of the regenerated cellulose membrane 160 with respect to molecule size as, e.g., maltodextrin is with an average weight of 1 kDa larger than glucose with a molecular weight of 180 Da.

Figure 7:
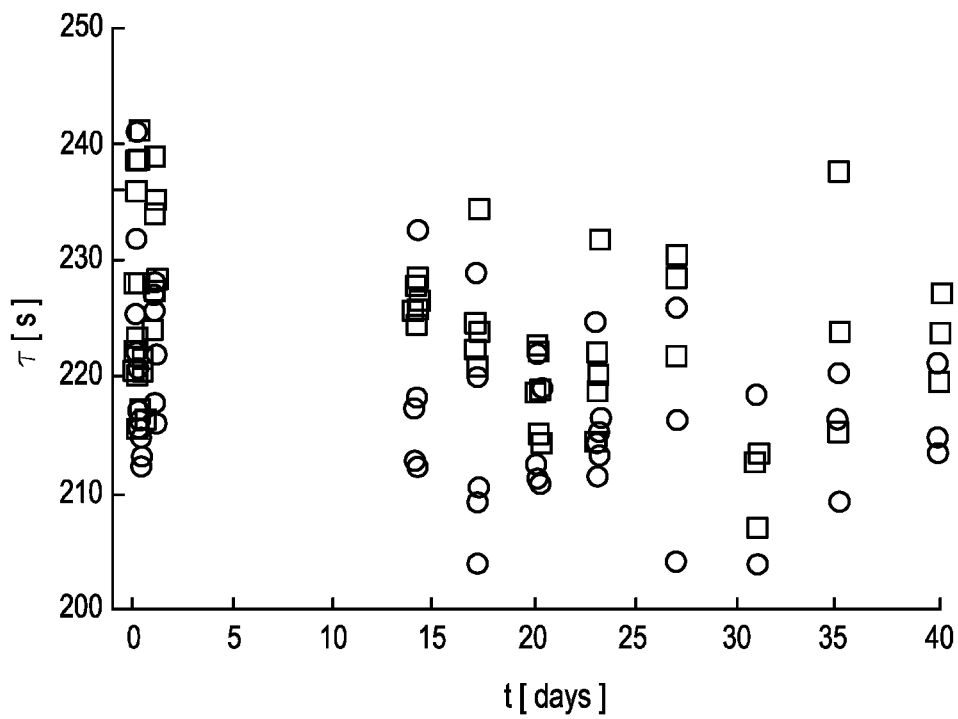
FIG. 7 shows experimental results of a long-term measurement of diffusion times of glucose using the sensor element with the biocompatible polymer membrane.

Specifically in order to investigate long-term stability of the system, FIG. 7 shows experimental results of a long-term measurement of diffusion times τ in seconds as a function of time tin days using of the sensor element 110 with the biocompatible polymer membrane 160 at room temperature. The same experimental as for FIG. 6 was used. For FIG. 7 the glucose diffusion time in the presence of 1000 mg/dL albumin was measured over a time period of 41 days. Therefore a solution with albumin only as well as a solution with albumin (1000 mg/dL) and glucose (500 mg/dL) were pumped in alternation into the reservoir and the respective diffusion curves were measured simultaneously. The circles indicate measurements where the glucose-albumin solution was pumped into the reservoir and the squares indicate measurements where albumin only solution was pumped into the reservoir. The diffusion time is observed to stay stable over the whole period of 41 days. The average is 225±15 s. Glucose diffusion into the measurement chamber 154 appears to be about 10 s faster compared to the diffusion of glucose out of the measurement chamber 154.

Figure 8:
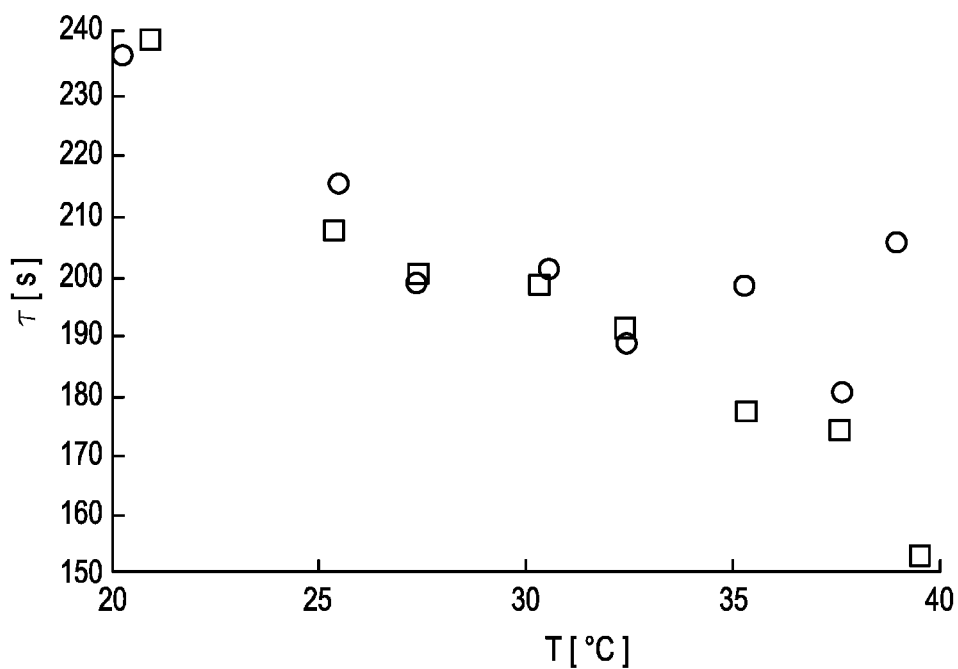
FIG. 8 shows experimental results of dependency of diffusion time of the sensor element with the biocompatible polymer membrane vs temperature.

FIG. 8 shows experimental results of dependency of diffusion time τ vs. temperature T in ° C. using the same experimental setup as for FIGS. 6 and 7. The squares indicate a measurement in which glucose diffuses out of the measurement chamber 154 and the circles indicate measurement in which glucose diffuses into the measurement chamber 154. In contrast to the measurements of FIGS. 4 and 5 which were measured without the biocompatible polymer membrane 160, an overall decrease in diffusion time with increasing temperature was observed. Specifically, comparing FIGS. 5 and 8 it can be observed that diffusion into the measurement chamber 154 takes longer compared to configurations without the biocompatible polymer membrane 160. However, these longer diffusion times can be accepted in view of the achieved long and stable life time in case of using the biocompatible polymer membrane 160. Furthermore, FIG. 8 exhibits that measurement at arbitrary temperatures is possible, in particular even at low temperatures.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 sensor element
112 Kit
114 measurement chamber plate
116 direction of diffusion
118 illumination source
120 illumination light beam
122 pulser device
124 rechargeable energy storage device
126 control unit
128 transfer device
130 reflection light beam
132 optical detector
134 evaluation device
136 amplifier circuit
138 memory unit
140 Housing
142 further device
144 communication unit
146 chamber wall
148 first chamber wall
150 first infrared window
152 second chamber wall
154 capillary element
156 spacer element
158 second infrared window
160 membrane element
162 attenuated total reflection element
164 Coating

What is claimed is:

1. A fully implantable sensor for detecting an analyte in a body fluid sample, comprising:
    a chamber plate configured to receive the body fluid sample, the chamber plate comprising a capillary formed between a first chamber wall and a second chamber wall and the chamber plate further comprising a biocompatible polymer membrane having a molecular weight cutoff of at least 15 kDa;
    a quantum cascade laser illumination source configured to generate an illumination light beam in a spectral range and to transmit the illumination light beam to the chamber plate, wherein when the illumination light beam at least partially illuminates the chamber plate, the chamber plate generates a reflection light beam that at least partially illuminates the body fluid sample within the chamber plate;
    an optical detector configured to detect at least one property of the reflection light beam and to generate a sensor signal dependent on the presence of the analyte; and
    a controller configured to evaluate the sensor signal.

2. The fully implantable sensor according to claim 1, wherein the biocompatible polymer membrane has a pore size in a range from 15 to 35 Å.

3. The fully implantable sensor according to claim 1, wherein the biocompatible polymer membrane comprises at least one polymer selected from the group consisting of: cellulose hydrate; nitrocellulose; polysulfone; polycarbonate; polyethersulfone; cellulose acetate; polyamide; and polytetrafluoroethylene.

4. The fully implantable sensor according to claim 3, wherein the polymer is hydrophilized.

5. The fully implantable sensor according to claim 1, wherein the biocompatible polymer membrane has a thickness in the range of from 1 to 250 μm.

6. The fully implantable sensor according to claim 1, wherein the quantum cascade laser is selected from the group consisting of: at least one fixed-frequency Fabry-Perot quantum cascade laser; at least one tunable external cavity quantum cascade laser; and at least one distributed feedback quantum cascade laser.

7. The fully implantable sensor according to claim 1, wherein the light beam has a wavelength in the infrared spectral range.

8. The fully implantable sensor according to claim 1, wherein the chamber plate has a chamber wall configured to receive the body fluid sample.

9. The fully implantable sensor according to claim 1, wherein the first chamber wall is at least partially transparent to the illumination light beam, wherein the first chamber wall has an at least partially transparent first infrared window.

10. The fully implantable sensor according to claim 9, wherein the second chamber wall is configured to receive the body fluid sample.

11. The fully implantable sensor according to claim 1, wherein the second chamber wall comprises an at least partially reflective second infrared window configured to permit transport of the analyte into the capillary element.

12. A kit for detecting an analyte in a body fluid sample, comprising:
- at least one fully implantable sensor according to claim 1; and
- an energy source configured to supply energy to a rechargeable energy storage device.

13. The kit according to claim 12, wherein the energy source is adapted to provide contactless electrical energy to the rechargeable energy storage device.

14. A method for detecting at least one analyte in a sample of body fluid, comprising:
- providing a fully implantable sensor in accordance with claim 1;
- receiving the sample of body fluid in the chamber plate;
- generating the illumination light beam and transmitting the illumination light beam to the chamber plate to at least partially illuminate the chamber plate;
- generating a reflection light beam in response to the illumination by the illumination light beam;
- at least partially illuminating the body fluid sample within the chamber plate with the reflection light beam;
- using the optical detector to detect at least one property of the reflection light beam and generating a sensor signal correlated to the presence of the analyte; and
- evaluating the sensor signal using the controller.

15. The fully implantable sensor according to claim 1, wherein the biocompatible polymer membrane has a thickness in the range of from 20 to 250 μm.

* * * * *